US006951727B2

(12) United States Patent
Davis

(10) Patent No.: US 6,951,727 B2
(45) Date of Patent: Oct. 4, 2005

(54) METHODS AND REAGENTS FOR QUANTITATION OF CELL-SURFACE MOLECULE EXPRESSION ON PERIPHERAL BLOOD CELLS

(75) Inventor: Kenneth A. Davis, Mountain View, CA (US)

(73) Assignee: Becton Dickinson and Company, Franklin Lakes, NJ (US)

(*) Notice: Subject to any disclaimer, the term of this patent is extended or adjusted under 35 U.S.C. 154(b) by 452 days.

(21) Appl. No.: 10/080,868

(22) Filed: Feb. 22, 2002

(65) Prior Publication Data

US 2002/0076734 A1 Jun. 20, 2002

Related U.S. Application Data

(63) Continuation of application No. 09/406,013, filed on Sep. 24, 1999, now Pat. No. 6,423,505, which is a continuation-in-part of application No. 09/204,860, filed on Dec. 3, 1998, now Pat. No. 6,200,766.

(51) Int. Cl.$^7$ ............................................. G01N 33/533
(52) U.S. Cl. ...................... 435/7.21; 435/961; 435/962; 435/975; 436/800; 436/808; 436/826
(58) Field of Search ............................... 435/7.21, 961, 435/962, 975; 436/800, 808, 826

(56) References Cited

U.S. PATENT DOCUMENTS

| | | | | |
|---|---|---|---|---|
| 4,337,063 | A | 6/1982 | Mihara et al. | 23/230 B |
| 4,404,289 | A | 9/1983 | Masuda et al. | 436/538 |
| 4,405,711 | A | 9/1983 | Masuda et al. | 435/4 |
| 4,654,312 | A | 3/1987 | Chang et al. | 436/519 |
| 4,876,190 | A | 10/1989 | Recktenwald | 435/7 |
| 4,902,613 | A | 2/1990 | Chang et al. | 435/2 |
| 5,268,486 | A | 12/1993 | Waggoner et al. | 548/427 |
| 5,426,028 | A | 6/1995 | Levy et al. | 435/7.24 |
| 5,510,267 | A | 4/1996 | Marshall | 436/63 |
| 5,516,695 | A | 5/1996 | Kim et al. | 436/17 |
| 5,547,849 | A | 8/1996 | Baer et al. | 435/7.24 |
| 5,556,764 | A | 9/1996 | Sizto et al. | 435/7.24 |
| 5,620,842 | A | 4/1997 | Davis et al. | 435/4 |
| 5,648,225 | A | 7/1997 | Kim et al. | 435/7.24 |
| 5,714,386 | A | 2/1998 | Roederer | 436/546 |
| 5,912,134 | A | 6/1999 | Shartle | 435/7.24 |
| 5,932,428 | A | 8/1999 | Dubrow et al. | 435/7.24 |
| 6,133,429 | A | 10/2000 | Davis et al. | 530/391.5 |
| 6,200,766 | B1 * | 3/2001 | Davis | 435/7.24 |

FOREIGN PATENT DOCUMENTS

| | | | | |
|---|---|---|---|---|
| EP | 0161770 B1 | 11/1991 | | G01N/33/50 |
| EP | 0747700 A2 | 12/1996 | | G01N/33/533 |
| WO | WO 98/35980 | 8/1998 | | C07H/21/02 |
| WO | WO 98/48017 | 10/1998 | | C12N/15/12 |

OTHER PUBLICATIONS

Vayuvegula et al, Jour, Clinical Immunology, 10, 247–254, 1990.*
Adorini, L. et al., "Competition for Antigen Presentation in Living Cells Involves Exchange of Peptides Bound by Class II MHC Molecules," *Nature*, 342(6251):800–803 (1989).
Asadullah, K. et al., "Immunodepression Following Neurosurgical Procedures," *Crit. Care Med.*, 23(12):1976–1983 (1995).
Becton Dickinson Immunocytometry Systems, "QuantiBRITE, Brilliance You Can Measure," 1–4 (1997).
Bone, R.C., "Sir Issac Newton, Sepsis, SIRS, and CARS," *Crit. Care Med.*, 24(7):1125–1128 (1996).
Bone, R.C., "Why Sepsis Trials Fail," *JAMA*, 276(7):565–566 (1996).
Cresswell, P., "Assembly, Transport, and Function of MHC Class II Molecules," *Annu. Rev. Immunol.*, 12:259–293 (1994).
Davis, K.A., "QuantiBRITE, A New Standard for Fluorescence Quantitation," Becton Dickinson Immunocytometry Systems, 1–15 (1997).
Deka, C. et al., "Analysis of Fluorescence Lifetime and Quenching of FITC–Conjugated Antibodies on Cells by Phase–Sensitive Flow Cytometry," *Cytometry*, 25(3):271–279 (1996).
Döcke, W.–D. et al., "Monocyte Deactivation in Septic Patients: Restoration by IFN–γ Treatment," *Nature Medicine*, 3(6):678–681 (1997).
Döcke, W.–D. et al., "Improvement of Monocyte Function–A New Therapeutic Approach?" in Reinhart et al. (eds.), *Sepsis: Current Perspectives in Pathophysiology and Therapy*, New York: Springer–Verlag (1994), pp 473–500.
Ernst, L.A. et al., "Cyanine Dye Labeling Reagents for Sulfhydryl Groups," *Cytometry*, 10(1): 3–10 (1989).
Fisher, C.J. et al., "Influence of an Anti–Tumor Necrosis Factor Monoclonal Antibody on Cytokine Levels in Patients with Sepsis," *Crit. Care Med.*, 21(3):318–327 (1993).
Fisher, C.J. et al., "Recombinant Human Interleukin 1 Receptor Antagonist in the Treatment of Patients with Sepsis Syndrome," *JAMA*, 271(23):1836–1843 (1994).
Fisher, C.J. et al., "Treatment of Septic Shock with the Tumor Necrosis Factor Receptor–Fc:Fusion Protein," *N. Engl. J. Med.*, 334(26):1697–1702 (1996).

(Continued)

*Primary Examiner*—David Saunders
(74) *Attorney, Agent, or Firm*—Douglas A. Petry

(57) ABSTRACT

Improved methods, reagents, and kits for quantitation of HLA-DR and/or CD11b expression on peripheral blood cells are presented. Inclusion of a lysosomotropic amine, such as chloroquine, during staining stabilizes HLA-DR and CD11b expression. Use of a novel anti-CD14 conjugate, anti-CD14-PerCP/CY5.5, permits the ready discrimination of monocytes. The improved methods, reagents, and kits may be used to assess immune competence, and to direct and monitor immunostimulatory therapies in septic patients exhibiting monocyte deactivation.

9 Claims, 12 Drawing Sheets

OTHER PUBLICATIONS

Hedin, U. et al., "Receptor–Mediated Endocytosis of Immunoglobulin–Coated Colloidal Gold Particles in Cultured Mouse Peritoneal Macrophages. Chloroquine and Monensin Inhibit Transfer of the Ligand from Endocytic Vesicles to Lysosomes," *Eur. J. Cell Biol.,* 39(1):130–135 (1985).

Hershmann, M.J. et al., "Interferon–Gamma Treatment Increases HLA–DR Expression on Monocytes in Severely Injured Patients," *Clin. Exp. Immunol.,* 77(1):67–70 (1989).

Kahan, M., "Detecting Intracellular Cytokines in Activated Monocytes," Application Note 2, Immune Function, Becton Dickinson Immunocytometry Systems, 1–12 (1997).

Kox, W.J. et al., "Interferon Gamma–1b in the Treatment of Compensatory Anti–Inflammatory Response Syndrome," *Arch. Intern. Med.,* 157(4):389–393 (1997).

Lansdorp, P.M. et al., "Single Laser Three Immunofluorescence Staining Procedures Based on Energy Transfer Between Phycoerythrin and Cyanine 5," *Cytometry,* 12(8):723–730 (1991).

Lavabre–Bertrand, T., "Flow–Cytometric Quantitation in Chronic Leukemias," *Eur. J. Histochem.,* 40/Suppl.1:33–38 (1996).

Liu, Z. et al., "Elevated Relative Fluorescence Intensity of CD 38 Antigen Expression on CD$^+$ T Cells in Marker of Poor Prognosis in HIV Infection: Results of 6 Years of Follow–Up," *Cytometry,* 26:1–7 (1996).

Moore, J.P., "Coreceptors: Implications for HIV Pathogenesis and Therapy," *Science,* 276:51–52 (1997).

Mujumdar, R.B. et al., "Cyanine Dye Labeling Reagents: Sulfoindocyanine Succinimidyl Esters," *Bioconj. Chem.,* 4(2):105–111 (1993).

Mujumdar, R.B. et al., "Cyanine Dye Labeling Reagents Containing Isothiocyanate Groups," *Cytometry,* 10(1):11–19 (1989).

Patel, T. et al., "A Fluorometric Assay for Quantitating DNA Strand Breaks During Apoptosis," *Anal. Biochem.,* 229(2):229–235 (1995).

Picker, L.J. et al., "Direct Demonstration of Cytokine Synthesis Heterogeneity Among Human Memory/Effector T Cells by Flow Cytometry," *Blood,* 86(4):1408–1419 (1995).

Polk, H.C. et al., "A Systematic Study of Host Defense Processes in Badly Injured Patients," *Ann. Surg.,* 204(3):282–299 (1986).

Poncelet, P. et al., "Quantitation of Hemopoietic Cell Antigens in Flow Cytometry," *Eur. J. Histochem.,* 40/suppl.1:15–32 (1996).

Rehse, M.A. et al., "Use of Fluorescence Threshold Triggering and High–Speed Flow Cytometry for Rare Event Detection," *Cytometry,* 272:317–322 (1995).

Reid, P.A. et al., "Cycling of Cell–Surface MHC Glycoproteins through Primaquine–Sensitive Intracellular Compartments," *Nature,* 346:655–657 (1990).

Roche, P.A. et al., "Cell Surface HLA–DR–Invariant Chain Complexes are Targeted to Endosomes by Rapid Internalization," *Proc. Natl. Acad. Sci. USA,* 90(18):8581–8585 (1993).

Schneider, Y.–J. et al., "Effect of Chloroquine and Methylamine on Endocytosis of Fluorescein–Labelled Control IgG and of Anti–(Plasma Membrane) IgG by Cultured Fibroblasts," *Eur. J. Biochem.,* 118(1):33–38 (1981).

Schultz, K.R. et al., "The Lysosomotropic Amines, Chloroquine and Hydroxychloroquine: A Potentially Novel Therapy for Graft–Versus–Host Disease," *Leukemia and Lymphoma,* 24(3/4):201–210 (1997).

Southwick, P.L. et al., "Cyanine Dye Labeling Reagents— Carboxymethylindocyanine Succinimidyl Esters," *Cytometry,* 11(3):418–430 (1990).

Suni, M.A. et al., "Detection of Antigen–Specific T Cell Cytokine Expression in Whole Blood by Flow Cytometry," *J. Immunol. Meth.,* 212:89–98 (1998).

van Vugt, M.J. et al., "Binding of PE–CY5 Conjugates to the Human High–Affinity Receptor for IgG (CD64)," *Blood,* 88(6):2358–2360 (1996).

Volk, H.–D. et al., "Monocyte Deactivation–Rationale for a New Therapeutic Strategy in Sepsis," *Inten. Care Med.,* 22(4):S474–S481 (1996).

Volk, H.–D. et al., "Alterations in Function and Phenotype of Monocytes from Patients with Septic Disease—Predictive Value and New Therapeutic Strategies," *Behring Inst. Mitt.,* (88):208–215 (1991).

Waggoner, A.S. et al., "PE–CY5, A New Fluorescent Antibody Label for Three–Color Flow Cytometry with a Single Laser," *Clinical Flow Cytometry,* Annals of the New York Academy of Sciences, A.L. Landy et al., eds., 677:185–193, (1993).

Watts, C., "Capture and Processing of Exogenous Antigens for Presentation on MHC Molecules," *Annu. Rev. Immunol.,* 15:821–850 (1997).

Young, H.A. et al., "Role of Interferon–γ in Immune Cell Regulation," *J. Leukocyte Biol.,* 58(4):373–381 (1995).

Zhao, Y.–X. et al., "The Dual Role of Interferon–γ in Experimental *Staphylococcus aureus* Septicaemia Versus Arthritis," *Immunology,* 93(1):80–85 (1998).

Kao, K. J., "Selective elution of HLA antigens and beta 2–microglobulin from human platelets by chloroquine diphosphate", *Transfusion,* vol. 28, No. 1, pp. 14–17(Jan.–Feb. 1988).

Mane, S. M. et al., "Purification and characterization of human lysosomal membrane glycoproteins", *Archives of Biochemistry and Biophysics,* vol. 268, No. 1, pp. 360–378 (Jan. 1989).

Minchinton, R. M. et al., "Evaluation and calibration of a fluorescence–activated cell sorter for the interpretation of the granulocyte immunofluorescence test (GIFT)", *Clinical and Laboratory Haematology,* vol. 11, No. 4, pp. 349–359, (1989).

* cited by examiner

Histogram Statistics

Log Data Units: Linear Va

Gate:G2    Gated Events:2282
Total Events:109882    X Parameter:FL2-H(Log)

| Marker | Left, Right | Events | Geo Mean | CV |
|---|---|---|---|---|
| All | 1, 9910 | 2282 | 181.41 | 167.55 |

PE molecule value: 6287

Histogram Statistics

Log Data Units: Linear Va

Gate:G2    Gated Events:2222
Total Events:101591    X Parameter:FL2-H(Log)

| Marker | Left, Right | Events | Geo Mean | CV |
|---|---|---|---|---|
| All | 1, 9910 | 2222 | 176.23 | 170.85 |

PE molecule value: 6111

METHODS AND REAGENTS FOR QUANTITATION OF CELL-SURFACE MOLECULE EXPRESSION ON PERIPHERAL BLOOD CELLS

CROSS REFERENCE TO RELATED APPLICATIONS

This application is a continuation U.S. patent application Ser. No. 09/406,013, filed Sep. 24, 1999, which issued as U.S. Pat. No. 6,423,505, which is a continuation-in-part of U.S. patent application Ser. No. 09/204,860, filed Dec. 3, 1998, which issued as U.S. Pat. No. 6,200,766, the disclosures of both of which are incorporated herein by reference in their entirety.

FIELD OF THE INVENTION

The present invention relates to improved methods, reagents and kits for quantitating the expression of HLA-DR and/or CD11b on the surface of human peripheral blood cells, particularly on the surface of peripheral blood monocytes. The invention further relates to methods for assessing immune competence and for directing and monitoring immunostimulatory therapies for sepsis based upon the levels of monocyte HLA-DR expression so measured.

BACKGROUND OF THE INVENTION

Sepsis is one of the most common causes of death in developed countries. Incidence is increasing, and mortality remains high.

Early efforts to understand sepsis and to intervene in the progressive multiorgan failure of septic shock focused upon readily observable physical, physiologic, and anatomic symptoms. To this day, the acute management of fever, infection, coagulatory dysfunction, vascular collapse and end-organ failure remains the standard of care.

More recent efforts, however, have focused upon immunologic mediators thought to underlie these systemic processes.

Animal models of sepsis have, for example, implicated a number of cytokines as mediators of the systemic inflammatory response seen early in the septic patient. In these models, acute parenteral challenge with endotoxin or with gram negative bacteria leads to production of tumor necrosis factor α (TNFα), interleukin-1 (IL-1), and gamma interferon (IFNγ). Gamma interferon has been shown to act synergistically with TNFα in inducing shock in these animals.

Yet recent efforts to treat sepsis by immunomodulation have proven disappointing. Attempts to reduce or ablate the effects of proinflammatory cytokines, particularly TNFα and IL-1, have not only failed to improve outcome, but have in several cases increased mortality. Fisher et al., *JAMA* 271:1836–43 (1994); Fisher et al., *N. Engl. J. Med.* 334:1697–1702 (1996); Fisher et al., *Crit. Care Med.* 21:318–327 (1993); reviewed in Bone, *JAMA* 276:565 (1996). There thus exists a need for immunomodulatory therapies that improve clinical outcomes in sepsis.

Recently, several observations have motivated an alternative, seemingly contrarian, immunomodulatory approach.

Acute bacterial invasion is in fact an atypical clinical presentation for human sepsis. In most patients, sepsis is a late complication of trauma, burn, or major surgery. Infections in these patients—coming late, as a secondary response to antecedent injury, rather than early, as the primary and actual cause of septic shock—bespeak a possible systemic immunosuppression or immune paralysis, rather than a state of hyperimmunity as predicted by the acute animal models.

In particular, studies have shown that HLA-DR expression by monocytes is severely depressed after trauma, and that such depressed levels correlate clinically with an increased susceptibility of trauma patients to infection. Polk et al., *Ann. Surg.* 204:282 (1986); Hershman et al., *Clin. Exp. Immunol.* 77:67–70 (1989).

Depression of monocytic HLA-DR expression has also been shown in a study of patients undergoing elective or emergent neurosurgery: patients who develop infectious complications in the postoperative period display a significantly lower level of monocytic HLA-DR expression than patients with an uncomplicated course; very low HLA-DR expression (fewer than 30 percent of peripheral blood monocytes positive for HLA-DR expression) predicts high risk for infection following surgery. Asadullah et al., *Crit. Care. Med.* 23:1976–1983 (1995).

Depression in HLA-DR expression has further been observed in the peripheral blood monocytes of septic patients with a wide variety of precipitating ailments. In these latter studies, surface immunophenotypic changes were further associated with decreased monocytic antigen-presenting function, reduced production of TNFα, IL-1 and IL6, anergy, and alterations in lymphocyte activity. Volk et al., *Behring Inst. Mitt.* 88:209–215 (1991); Döcke et al., in Reinhart et al. (eds.), *Sepsis: Current Perspectives in Pathophysiology and Therapy*, New York: Springer-Verlag (1994) pp 473–500.

Monocytes, like macrophages, B cells, and dendritic cells, are "professional" antigen presenting cells (APCs). Although a number of cell types are capable of processing soluble antigens for subsequent display to T lymphocytes, the so-called "nonprofessional" APCs lack the accessory molecules required to complete the process of T cell activation. "Professional" antigen-presenting cells, such as monocytes, not only process and present antigens in the context of MHC, but also possess the additional accessory molecules required to complete T cell activation, rendering them critical to the development of a full T cell-directed immune response. Reversal of monocytic deactivation in late-stage sepsis might, therefore, be expected to improve immune function, conferring clinical benefit.

Gamma interferon (IFNγ) is a major activator of monocytes. It upregulates the surface expression of costimulatory and HLA molecules, increasing monocyte antigen-presenting capacity, and primes for the LPS-induced production of proinflammatory cytokines. Young et al., *J. Leukocyt. Biol.* 58:373–381 (1995).

A single clinical trial of gamma interferon treatment of late-stage sepsis has been reported. Peripheral blood monocyte HLA-DR levels were monitored in patients meeting the inclusion criteria for severe sepsis. Gamma interferon was administered to those patients in whom, over two consecutive days, fewer than 30% of peripheral blood monocytes measured positive for HLA-DR expression. Treatment was continued until the percentage of monocytes with demonstrable HLA-DR expression remained over 50% for three days. Of the 10 patients, 8 showed an increase in monocyte HLA-DR expression within 1 day of treatment; the other 2 responded within 2 to 3 days. The recovery of monocytic HLA-DR expression was associated with restitution of monocytic function in vivo, as evidenced by a significant increase of TNFα and IL-6 plasma levels during treatment and a more favorable clinical outcome. Kox et al., *Arch.*

*Intern. Med.* 157:389–393 (1997); Döcke et al., *Nature Med.* 3:678–680 (1997).

Because administration of a proinflammatory cytokine would be contraindicated, however, in the early, hyperimmune phase of sepsis, there exists a need for a rapid, reliable method for measuring HLA-DR expression on peripheral blood monocytes. There further exists a need for a method that would report values for a given peripheral blood sample that are reliable and substantially independent of the individual testing laboratory.

Typically, as in the reported clinical study, monocyte HLA-DR expression is assessed flow cytometrically. Monocytes are distinguished from other peripheral blood cells by either surface immunophenotype, physical properties (side scatter and/or forward scatter), or some combination thereof; HLA-DR levels are assessed on the monocytes so distinguished by use of a fluorophore-conjugated anti-HLA-DR antibody.

Monocytes may, for example, be distinguished using an antibody specific for CD14. CD14, a receptor for lipopolysaccharide, is expressed predominantly on cells of the myelomonocytic lineage; in peripheral blood, CD14 is expressed principally by monocytes. But granulocytes in the blood also react with anti-CD14 antibodies, albeit weakly, and with present anti-CD14 conjugates cannot be completely discriminated from monocytes. Gating out $CD14^{dim}$ cells, as a means of removing granulocytes from the analysis, removes $CD14^{dim}$ monocytes as well, confounding the HLA-DR analysis. There thus exists a need for a fluorophore that, when conjugated to anti-CD14 antibody, would permit the immunocytochemical discrimination of monocytes from granulocytes.

HLA-DR may readily be labeled on the surface of peripheral blood cells, including monocytes, using a fluorophore-conjugated anti-HLA-DR antibody. But the surface expression of HLA-DR on the surface of monocytes is not a simple, static, and stable phenotype. MHC restriction imposes conflicting demands on the protein processing machinery of the APC: on the one hand, there is a requirement for proteolytically-processed peptide antigen; on the other, there is a requirement for intact MHC class II protein. These concurrent requirements are met by a finely choreographed, and as yet incompletely understood coordinated movement of endocytosed antigen and newly-synthesized MHC class II molecules through various internal compartments of the cell. Cresswell, *Annu. Rev. Immunol.* 12:259–93 (1994). Rapid recycling of class II molecules from the surface, through compartments in part distinct from those traversed by newly-synthesized MHC, and then back to the surface, implicates yet other, likely intersecting, intracellular pathways. Reid et al., *Nature* 346:655–657 (1990); Roche et al., *Proc. Natl. Acad. Sci. USA* 90:8581–85 (1993); Watts, *Annu. Rev. Immunol.* 15:821–50 (1997).

The level of HLA-DR-specific fluorescence reported by peripheral blood monocytes depends upon the duration of incubation with anti-HLA-DR antibody, evidence of the dynamic nature of HLA-DR expression. This time dependence makes reliable absolute measurements of HLA-DR expression difficult. There thus exists a need for a method and reagents that would permit the stabilization of HLA-DR levels for flow cytometric assay.

SUMMARY OF THE INVENTION

The present invention solves these and other problems in the art by providing improved methods, reagents, and kits for quantitating the expression of HLA-DR and/or CD11b on the surface of human peripheral blood cells, particularly on the surface of peripheral blood monocytes.

The invention is based, in part, upon the novel finding that including chloroquine during staining of peripheral blood with anti-HLA antibody stabilizes the HLA-DR-specific signal obtained from $CD14^+$ monocytes. This is surprising: chloroquine has been reported to be unable to block the cellular recycling of MHC glycoproteins, and other agents that affect protein processing, such as Brefeldin A and monensin, have been shown ineffective in stabilizing HLA-DR expression. Equally surprising is the novel finding that including chloroquine during staining of unfractionated peripheral blood with anti-CD11b antibody stabilizes the CD11b-specific signal.

The invention is also based in part upon the finding that conjugation of an anti-CD14 antibody to a fluorescence energy resonance transfer tandem fluorophore, PerCP/CY5.5, provides a high intensity, highly uniform and clustered signal from peripheral blood monocytes, permitting the ready discrimination of monocytes from granulocytes. Incorporating these improvements provides an assay well-suited for clinical use, permitting the rapid and reliable quantitative measurement of peripheral monocytic HLA-DR levels.

In a first aspect, therefore, the present invention provides a method of measuring HLA-DR expression on the surface of human blood cells, comprising contacting a sample containing human blood cells with a lysosomotropic amine and an antibody specific for HLA-DR, and then detecting the binding of the anti-HLA-DR antibody to the cells. In preferred embodiments, the lysosomotropic amine is chloroquine. In preferred embodiments, the anti-HLA-DR antibody is conjugated to a fluorophore, preferably at a defined molar ratio; particularly preferred is conjugation to PE at a defined molar ratio, and especially preferred is conjugation to PE at a molar ratio of 1:1.

The invention also provides for the measurement of HLA-DR on the surface of peripheral blood monocytes. In preferred embodiments, a monocyte-distinguishing antibody, typically anti-CD14, is included in the staining step. In particularly preferred embodiments, the anti-CD14 antibody is conjugated to the PerCP moiety of a PerCP/CY5.5 tandem fluorophore molecule, permitting single-laser, multicolor flow cytometric analysis.

In preferred embodiments, a whole blood sample is employed, although the methods and reagents may equally be used with appropriate blood fractions, such as fractions enriched in peripheral blood mononuclear cells. In the whole blood embodiments, a further step of lysing the erythrocytes in the blood sample preferably intervenes between the staining step and the detection step. The method may include yet a further step of removing lysis debris after the lysis step but before detection.

Results from the improved HLA-DR assay of the present invention correlate well with results from prior, but problematic, assays. This high degree of correlation permits the direct translation of the established clinical criteria to measurements reported by the present assay.

Thus, in another aspect, the present invention provides a method of assessing the immune status of a human patient, comprising the steps of contacting a sample containing the patient's blood cells with a lysosomotropic amine and an antibody specific for HLA-DR; detecting the binding of the anti-HLA-DR antibody to the monocytes in the sample; and then comparing the level of binding so detected with that so detected from human controls. In preferred embodiments of this method, the lysosomotropic amine is chloroquine, the anti-HLA-DR antibody is conjugated to PE, and a monocyte-distinguishing antibody, such as anti-CD14, preferably anti-CD14-PerCP/CY5.5, is included in the staining step.

The invention also provides, in a related aspect, a method for determining the suitability of immunostimulatory therapy in a patient with sepsis, comprising contacting a sample containing the patient's blood cells with a lysosomotropic amine and an antibody specific for HLA-DR; detecting the binding of the anti-HLA-DR antibody to the monocytes in the sample; and then comparing the level of binding so detected with that detected from normal controls. Patients with levels of binding less than that of controls are determined to be suitable for immunostimulatory treatment. Applying present clinical criteria, sepsis patients averaging fewer than 5000 anti-HLA-DR antibodies per monocyte are determined to be suitable for immunostimulatory treatment, with patients averaging fewer than 3000 anti-HLA-DR antibodies per monocyte determined to be particularly suitable, and with patients averaging fewer than 3000 anti-HLA-DR antibodies per monocyte for two consecutive days determined to be especially suitable for immunostimulatory treatment.

In especially preferred embodiments of the method for determining the suitability of treatment, a peripheral blood sample is in the first step contacted with an anti-HLA-DR PE antibody, an anti-CD14-PerCP/CY5.5 antibody, and chloroquine.

In another aspect, the present invention provides compositions for performing the subject methods. The compositions for flow cytometric measurement of HLA-DR on human peripheral blood cells comprise a fluorophore-conjugated anti-HLA-DR antibody and a lysosomotropic amine, preferably chloroquine. The anti-HLA-DR antibody is preferably conjugated to PE, most preferably at a defined molar ratio, and in especially preferred embodiments, at a molar ratio of 1:1.

For flow cytometric measurement of HLA-DR on peripheral blood monocytes, the compositions of the present invention further comprise a monocyte-distinguishing antibody, preferably an anti-CD14 antibody, more preferably an anti-CD14 antibody conjugated to a fluorescence energy transfer tandem fluorophore, most preferably conjugated to the PerCP moiety of PerCP/CY5.5.

The present methods are particularly useful in clinical settings and will thus likely be performed, inter alia, by clinical laboratories. However, any one clinical laboratory may have only sporadic need to perform such methods. The invention thus provides, in another aspect, kits that permit the assay readily to be performed on an as-needed basis.

In preferred embodiments, a kit of the present invention comprises one or more staining compositions and an erythrocyte-lysing composition. At least one staining composition comprises an anti-HLA-DR antibody and a lysosomotropic amine, preferably chloroquine. In preferred embodiments, the anti-HLA-DR antibody is conjugated to PE, preferably at a defined molar ratio, most preferably at a ratio of 1:1. In embodiments useful for quantitating HLA-DR on the surface of peripheral blood monocytes, at least one staining composition of the kit comprises a monocyte-distinguishing antibody, preferably anti-CD14. In preferred embodiments, the anti-CD14 antibody is conjugated to a fluorescence resonance transfer tandem fluorophore, most preferably PerCP/CY5.5. In particularly preferred embodiments, the kit contains a staining composition that comprises an anti-HLA-DR-PE antibody, an anti-CD14-PerCP/CY5.5 antibody, and chloroquine.

In other embodiments, the kit comprises one or more staining compositions, an erythrocyte lysing composition, and further comprises pelletized beads conjugated with defined levels of PE. In these embodiments, the anti-HLA-DR antibody is conjugated to PE and the pelletized beads permit the calibration of the flow cytometer to allow quantitation, from the measured PE fluorescence, of the amount of HLA-DR antibody bound per cell.

In another aspect, the invention provides a novel monocyte-specific immunoconjugate, comprising an anti-CD14 antibody conjugated to the PerCP moiety of a PerCP/CY5.5 tandem dye molecule. The specificity of the CY5.5 moiety for CD64, coupled with the specificity of the antibody for CD14, provides a high intensity monocyte-specific signal for single laser, multicolor fluorescence activated cell sorting applications.

In yet another aspect, the invention provides an improved method of measuring CD11b expression on the surface of human blood cells, comprising contacting a sample containing human blood cells with a lysosomotropic amine and an antibody specific for CD11b; and then detecting the binding of the CD11b antibody to the cells.

BRIEF DESCRIPTION OF THE DRAWINGS

The above and other objects and advantages of the present invention will be apparent upon consideration of the following detailed description taken in conjunction with the accompanying drawings, in which.

DETAILED DESCRIPTION OF THE INVENTION

In the description, the following term is used. "Monocyte-distinguishing antibody" refers to any antibody that may be used alone, in combination with a cell's physical properties, such as light-scattering properties, or in combination with one or more additional antibodies, to distinguish monocytes in a peripheral blood sample. The term thus includes, inter alia, an anti-CD14 antibody.

Recent clinical studies suggest that proinflammatory cytokines, such as IFN-γ and G-CSF, may be used successfully to treat those septic patients in whom the early, proinflammatory response has given way to a systemic immunosuppression, also termed an "immune paralysis". Further evidence suggests that persistent reduction in HLA-DR expression on peripheral blood monocytes is a useful clinical marker of this immunosuppressed state, and that therapeutic decisions may successfully be based upon such measurements.

Although reagents and methods presently exist that permit the measurement of HLA-DR on the surface of monocytes, two problems readily attend attempts to develop an improved flow cytometric assay that is at once rapid, reproducible, and quantitative.

Figure 1:
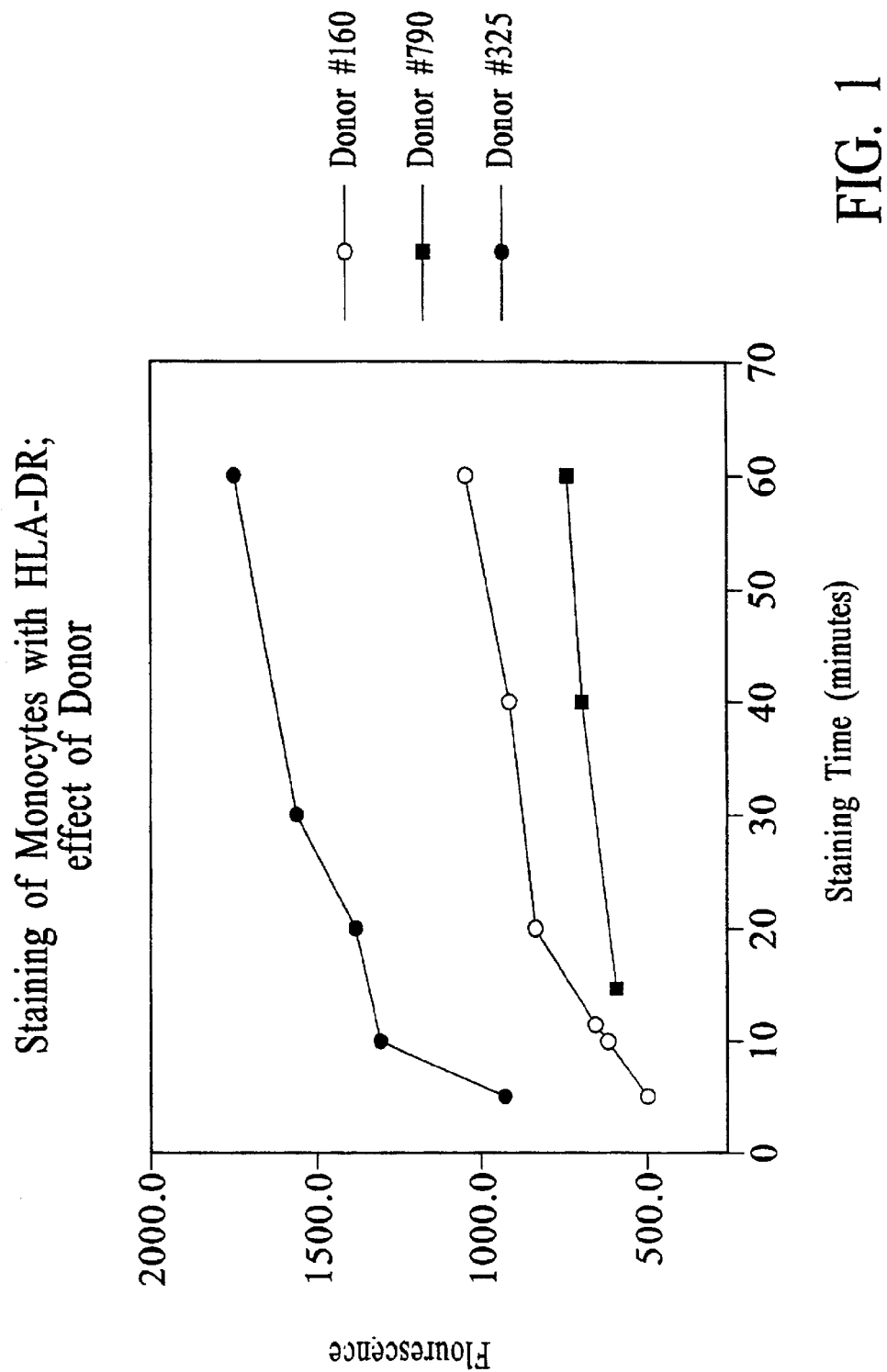
FIG. 1 is a graph demonstrating the time-dependence of HLA-DR-specific fluorescent signal reported by $CD14^+$ monocytes incubated for increasing times with an anti-HLA-DR antibody.

The first relates to the dynamic nature of HLA-DR expression on the surface of professional APCs such as monocytes. As further described below in Example 1, peripheral blood samples from normal donors were incubated with a commercially-available PE-conjugated anti-HLA-DR antibody. Also present in the incubation was a monocyte-distinguishing antibody, anti-CD14. FIG. 1 demonstrates that the incubation of peripheral blood samples with an anti-HLA-DR antibody gives rise to a time-dependent increase in HLA-DR-specific fluorescence measured flow cytometrically on the $CD14^+$ monocytes. Furthermore, the slope of the increase depends upon the individual donor; as a result, it cannot readily be controlled by a simple and universal mathematical adjustment.

The basis for this time-dependence of HLA-DR fluorescence signal is uncertain.

Part of the mechanistic uncertainty no doubt derives from the ability of the flow cytometer readily to detect fluorescence from internalized, as well as cell surface-bound, antibody. Picker et al., *Blood* 86(4):1408–1419 (1995); Suni et al., *J. Immunol.* 212:89–98 (1998). MHC class II antigens are known to be internalized and then recycled. The process is rapid, with a half-time for endocytosis of the surface class II population of 33 minutes; recycling traffic may in fact exceed HLA-DR biosynthetic traffic by some 60-fold. Reid et al., *Nature* 346:655–57 (1990). While not wishing to be bound by theory, it is possible that the increase in HLA-DR signal that is observed is occasioned by the progressive internal accumulation of protein labeled during its passage on the cell surface.

Uncertainty also derives from the very complexity of the trafficking routes. Class II MHC glycoproteins traverse a number of intracellular compartments during biosynthetic maturation, Cresswell, *Annu. Rev. Immunol.* 12:259–93 (1994), and recycling occurs through disparate, but likely intersecting, pathways. Watts, *Annu. Rev. Immunol.* 15:821–50 (1997).

The present invention is based in part upon the surprising finding that chloroquine, when included in the incubation with anti-HLA antibody, stabilizes the HLA-DR-specific signal obtained from $CD14^+$ monocytes. This finding is particularly surprising given chloroquine's reported inability to block the recycling of MHC glycoproteins, Reid et al., *Nature* 346:655–57 (1990).

FIG. 2 demonstrates that addition of chloroquine at a final concentration of 3 mM stabilizes the HLA-DR fluorescence signal. Azide (FIG. 2A), Brefeldin A (FIG. 2C) and monensin (FIG. 2C), the latter two of which are known to interfere with Golgi-related protein processing steps, provide no significant stabilization.

Thus, inclusion of chloroquine during the incubation with anti-HLA-DR antibody renders the result substantially independent of the duration of incubation, from approximately 15 minutes up to the maximum tested period of 60 minutes. This substantially increases the reliability, reproducibility, and utility of this assay for clinical use.

Although the incubation shown in FIG. 2 ranges from about 15 minutes to about 60 minutes, incubation is preferably 20–50 minutes, more preferably 25–45 minutes, most preferably 25–35 minutes. And although chloroquine is exemplified and presently preferred, other lysosomotropic amines that stabilize the HLA-DR-specific fluorescent signal may also be used. Lysosomotropic amines include, e.g., chloroquine, hydroxychloroquine, primaquine, and methylamine.

Figure 2A:
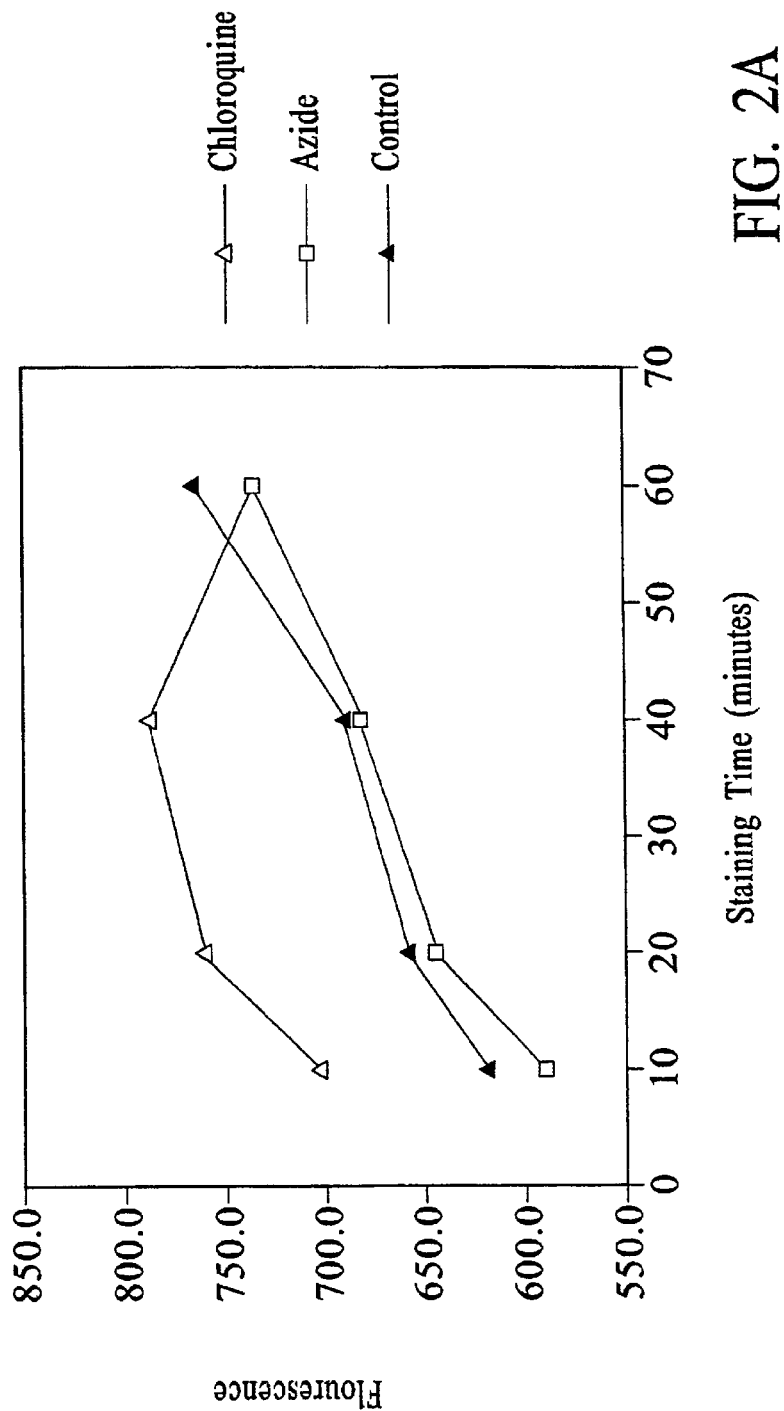
FIG. 2 presents graphs demonstrating the ability of chloroquine—but not of azide, Brefeldin A or monensin—to stabilize the HLA-DR-specific fluorescent signal measured flow cytometrically from monocytes of different individuals, with FIGS. 2D and 2E showing the results of chloroquine titration experiments.
Figure 2B:
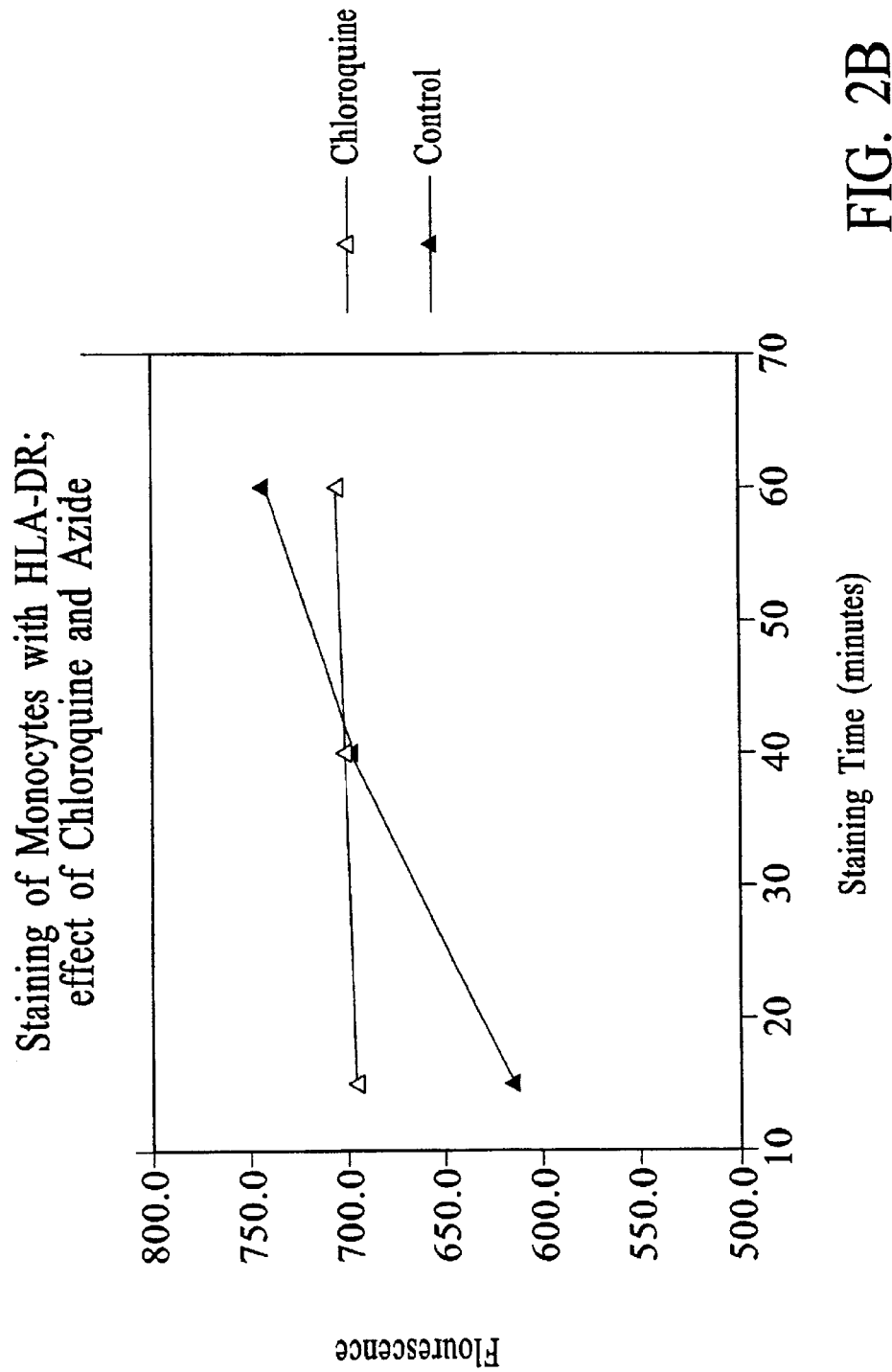
Figure 2C:
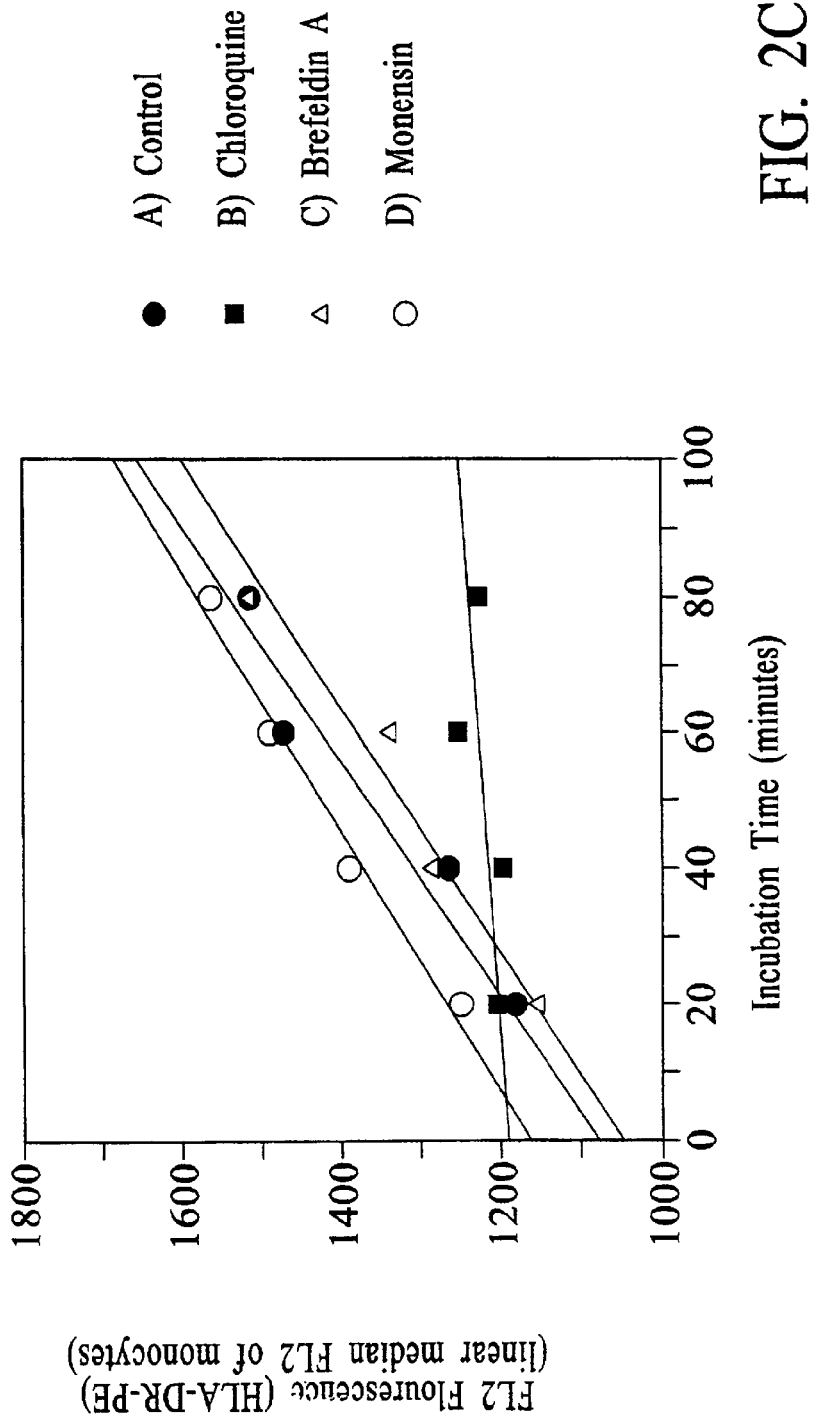
Figure 2D:
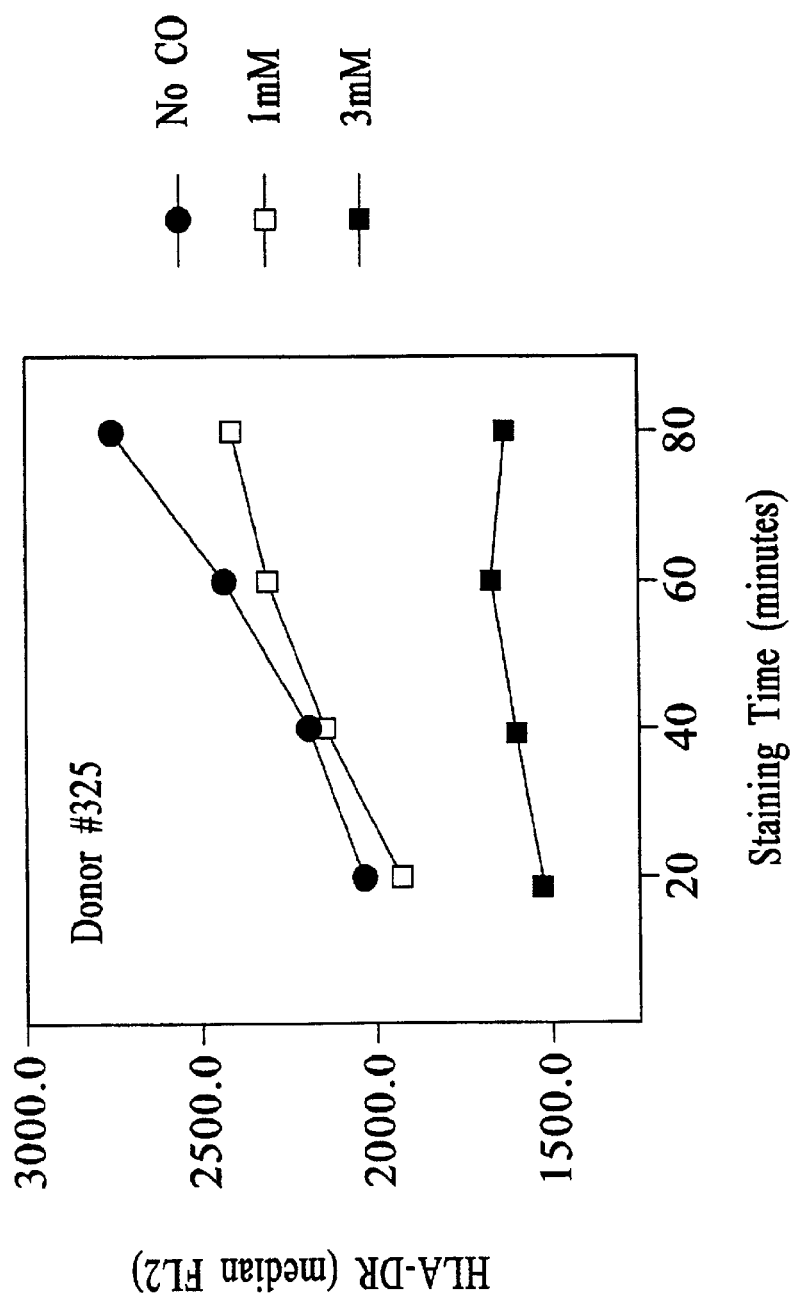
Figure 2E:
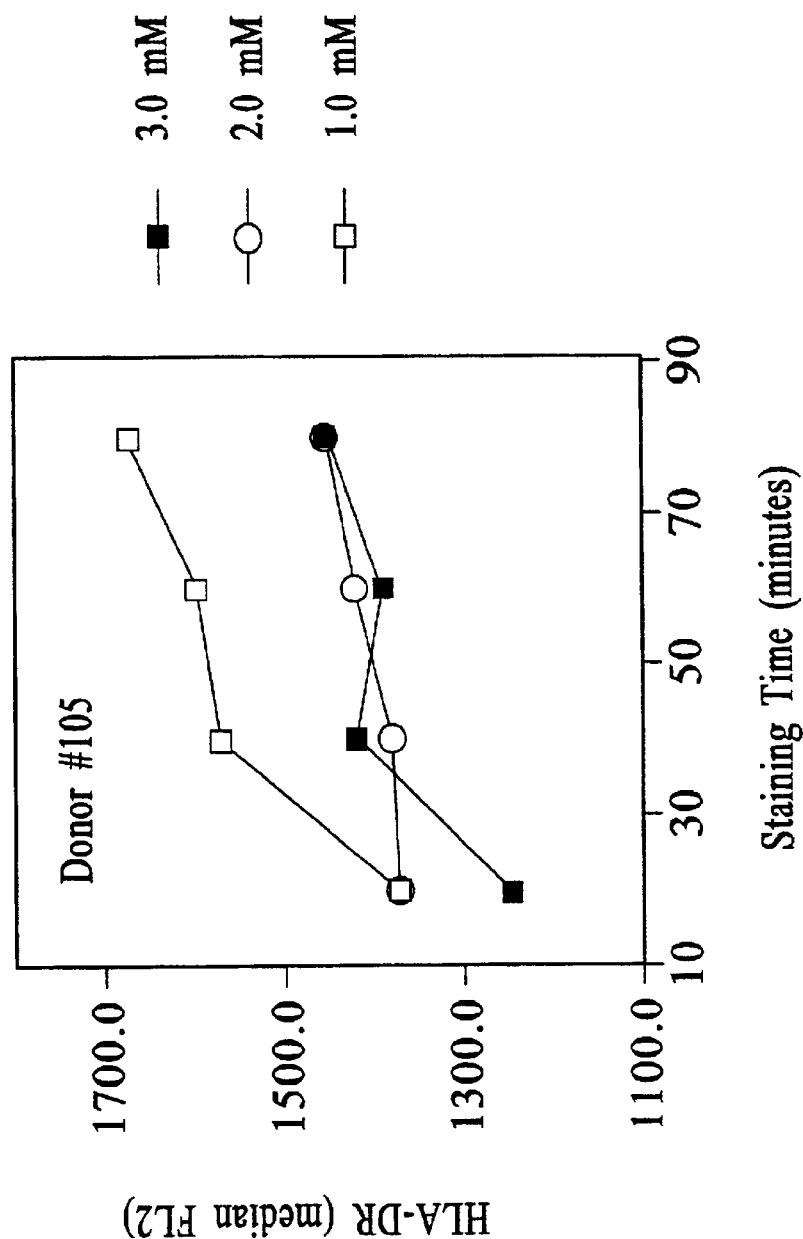

FIGS. 2D and 2E present chloroquine titration experiments, demonstrating that a minimum concentration of 2 mM chloroquine is needed to effect HLA-DR stabilization in the assay. Chloroquine is thus included in the incubation at a final concentration of 2.0–50 mM, preferably 2–5 mM, more preferably at a final concentration of 2–3 mM, most preferably at a final concentration of about 3 mM. Determination of concentration of chloroquine or other lysosomotropic amine that is best suited to the stable measurement of HLA-DR is readily determined using standard titration experiments, such as are reported in Example 2, below.

In preferred embodiments of the method and reagents of the present invention, the anti-HLA-DR antibody is specific for nonpolymorphic class II determinants, and may thus be used for measurement of HLA-DR in multiple individuals, preferably all human individuals. It is also preferred that the antibody not cross-react with HLA-DQ or HLA-DP molecules. The experiments reported herein used anti-HLA-DR antibodies from clone L243.

In addition, although the methods of the present invention may use a variety of anti-HLA-DR antibodies conjugated to a variety of fluorophores, a preferred embodiment of the methods of the present invention utilizes HLA-DR antibodies that permit the quantitation of HLA-DR surface density.

A number of recent reports demonstrate the advantages of measuring the amount, or density, of antigen expression on cell populations, as compared with simply assaying the frequency of cells expressing the antigen. Poncelet et al., *Eur. J. Histochem.* 1:15–32 (1996); Lavabre-Bertrand, *Eur. J. Histochem.* 1:33–38 (1996); Liu et al., *Cytometry* 26:1–7 (1996); Moore, *Science* 276:51–52 (1997); Rehse et al., *Cytometry* 22: 317–322 (1995); Patel et al., "*Anal. Biochem.* 229:229–235 (1995). Quantitative methodology is especially important in characterizing cell populations that express heterogeneous levels of antigen and in characterizing expression of antigens whose levels change dynamically. Monocyte expression of HLA-DR meets both these criteria.

In the context of immunostimulatory treatment of sepsis, finer discrimination of monocytic HLA-DR surface levels should lead to more accurate and improved discrimination of the patient populations likely to benefit from therapy, avoiding immunostimulation of clinically inappropriate patients. As to those patients selected for treatment with IFN-γ, G-CSF, or other immunostimulants, finer discrimination of monocytic HLA-DR levels should permit dosage individualization based upon the density distribution of HLA-DR on each patient's peripheral blood monocytes; in the reported pilot study, all patients meeting the inclusion criteria were given a uniform dose of interferon.

Yet a further advantage of quantitative analysis is that such quantitation renders the assay essentially independent of laboratory to laboratory variation. In contrast, qualitative classification, such as defining positively-staining populations as bright or dim, is both subjective and highly dependent upon the measuring instrument and its settings. For example, in the clinical trial reported by both Kox et al., Arch. Intern. Med. 157:389–393 (1997) and Döcke et al., Nature Med. 3:678–681 (1997), the PE fluorescence intensity cutoff used to distinguish the HLA-DR$^-$ from HLA-DR$^+$ populations was both idiosyncratic and machine-dependent. Additionally, the use of such a criterion to define two populations, one positive, one negative, provides only a crude measure of the distribution of HLA-DR densities in the monocyte population.

Thus, a preferred embodiment of the compositions, methods and kits of the present invention utilize HLA-DR antibodies that permit the quantitation of HLA-DR surface density. Preferably, such antibodies are conjugated to phycoerythrin (PE), more preferably at a defined PE:Ab molar ratio, most preferably at a 1:1 molar ratio.

PE is particularly well-suited to such quantitative analysis: it is bright, and it does not self-quench. Fluorophores such as fluorescein isothiocyanate (FITC), CY3 and CY5 can self-quench due to overlap of their excitation and emission spectra. Quenching of FITC has been shown to occur both through proximity of FITC molecules on a single antibody and through the proximity of FITC molecules on adjacent antibodies directed to a high density cellular epitope. Haugland, *Handbook of Fluorescent Probes and Research Chemicals,* 6th ed., Molecular Probes Inc., Eugene, Oreg. (1996); Deka et al., *Cytometry* 25:271–279 (1996). Peridinium chlorophyll protein (PerCP), which is described, inter alia, in U.S. Pat. No. 4,876,190, incorporated herein by reference, photolyses during its transit through the laser of the flow cytometer, precluding accurate quantitation. Other advantages of PE for antigen density quantitation are described in U.S. Pat. No. 5,620,842, incorporated herein by reference.

A further advantage of PE as a fluorophore is the commercial availability of anti-HLA-DR antibodies conjugated at defined molar ratios of PE (Becton Dickinson Immunocytometry Systems, San Jose, Calif.) and the commercial availability of pelletized bead standards (QuantiBRITE™, BDIS), the beads providing defined levels of PE fluorescence.

Figure 3A:
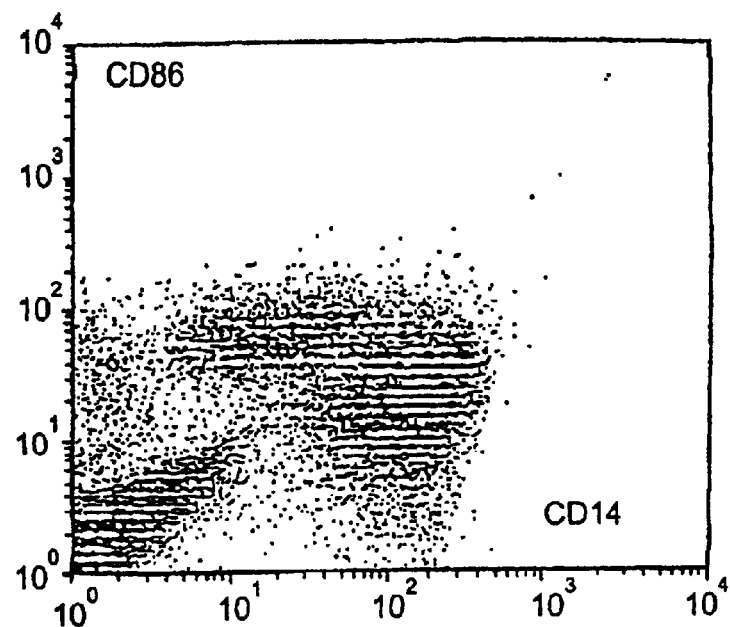
FIG. 3 shows dot plots of peripheral blood cells from two individuals, demonstrating wide range of CD14-specific FITC fluorescence in the $CD86^+$ population.
Figure 3B:
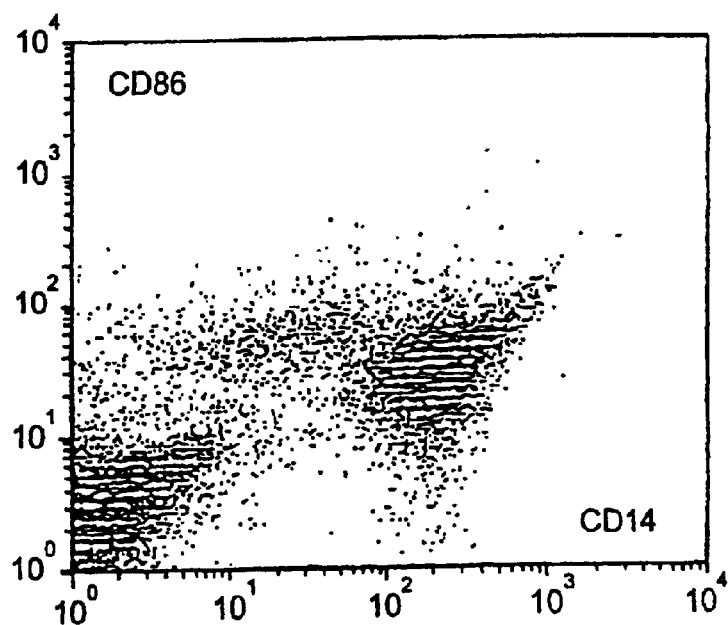

The second problem encountered in attempts to develop an improved flow cytometric assay for HLA-DR expression on peripheral blood monocytes is that anti-CD14 antibodies labeled with FITC and with other common, PE-distinguishable, fluorophores do not permit the unambiguous discrimination of monocytes from granulocytes. A sufficient percentage of monocytes stain dimly with anti-CD14 as to overlap the weakly-stained granulocytic population. This is shown in FIG. 3, dot plots from two separate patients demonstrating, in each case, the wide range of anti-CD14-FITC fluorescence in the CD86$^+$ population in peripheral blood.

The present invention is based, in part, upon the novel finding that conjugating an anti-CD14 antibody to the PerCP moiety of a PerCP/Cy5.5 resonance energy transfer tandem fluorophore provides a highly specific, highly uniform, high intensity clustered signal from peripheral blood monocytes, permitting the ready discrimination of monocytes from granulocytes.

Cyanine resonance energy transfer tandem fluorophores ("tandem fluorophores", "tandem dyes", "tricolor stains") have recently expanded the choices of fluorophore available for single-laser, multi-color flow cytometric analysis. PE-CY5 tandem staining proves particularly well-suited for three-color analysis: the R-PE moiety, excited by the 488 nm light of an argon ion laser, serves as an energy donor, and CY5, acting as an energy acceptor, fluoresces at 670 nm, readily distinguishable from the emission of FITC and PE. Cyanine fluorophores are described in U.S. Pat Nos. 5,268, 486; 4,337,063; 4,404,289; 4,405,711; and in Mujumdar et al., *Bioconj. Chem.* 4:105–111 (1993); Southwick et al., *Cytometry* 11:418–430 (1990); Ernst et al., *Cytometry* 10:3–10 (1989); and Mujumdar et al., *Cytometry* 10:11–19 (1989), and cyanine energy resonance transfer tandem fluorophores are described, inter alia, in U.S. Pat. No. 5,714,386 and in Waggoner et al., *Ann. NY Acad. Sci.* 677:185–193 (1993) and Lansdorp et al., *Cytometry* 12:723–30 (1991), the disclosures of which are incorporated herein by reference.

However, the CY5 moiety of these tandem fluorophores has been shown to bind directly to CD64 (FcγRI) giving spurious, antibody-independent, signals on CD64$^+$ cells. van Vugt et al., *Blood* 88:2358–2360 (1996). This antibody-independent binding has motivated considerable efforts in the art to mask the CY5 moiety to reduce the spurious binding to CD64 molecules presented on the surface of peripheral blood cells as described, inter alia, in U.S. patent application Ser. No. 08/943,491, filed Oct. 3, 1997, which issued as U.S. Pat. No. 6,133,429, the disclosure of which is incorporated herein by reference in its entirety.

But CD64 is constitutively expressed on monocytes and macrophages, and is strongly up-regulated by IFN-γ, making it a useful monocyte-distinguishing marker.

Reversing prior art efforts to bring the CY5 moiety into increasing proximity to the antibody to mask its CD64 specificity, a novel anti-CD14 conjugate was prepared in which the CY5.5 moiety of a tandem PerCP/CY5.5 fluorophore was purposely oriented to facilitate its interaction with CD64. In this conjugate, the anti-CD14 antibody was conjugated to the PerCP moiety of a PerCP/CY5.5 tandem dye, thus displaying the CY5.5 moiety at some distance from the antibody.

Figure 4A:
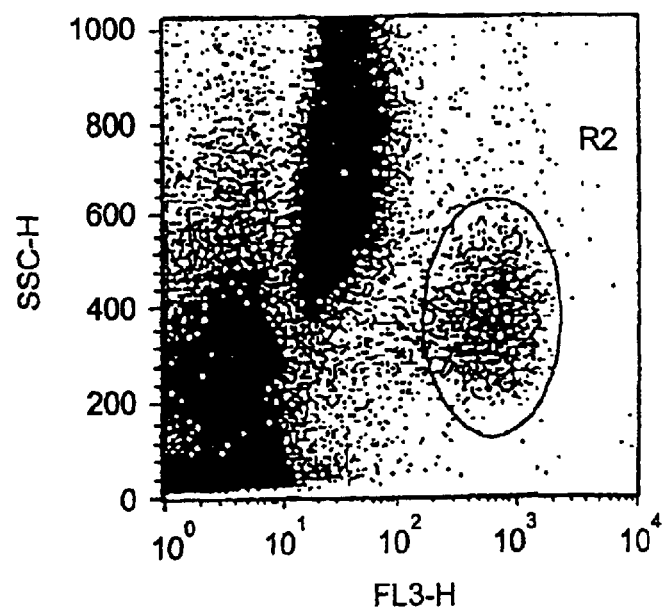
FIG. 4 shows dot plots of peripheral blood cells drawn from the same two individuals as in FIG. 3, demonstrating strong clustering of $CD14^+$ monocytes (circled) using an anti-CD14 antibody conjugated to the PerCP moiety of a PerCP/CY5.5 tandem fluorophore.
Figure 4B:
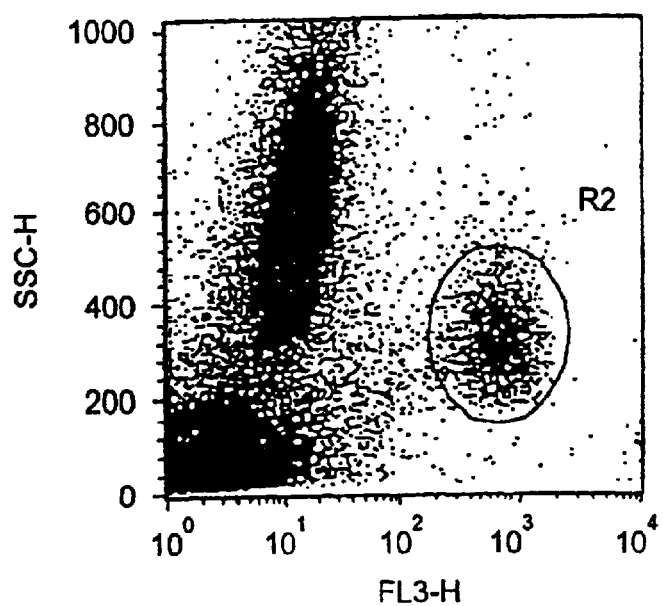

FIG. 4 shows the strong clustering of CD14$^+$ monocytes observed using this novel CD14-PerCP/CY5.5 conjugate. The samples are drawn from the same patients as those for whom data is shown in FIG. 3. Although PerCP/CY5.5 is exemplified, the tandem fluorophore PE/CY5 may also be used. PerCP/CY5 has been found ineffective in the present methods.

In one aspect, then, the instant invention provides a method of measuring HLA-DR surface expression on human peripheral blood monocytes that incorporates both of these improvements. In preferred embodiments, a peripheral blood sample is contacted in the presence of chloroquine with a first antibody, the first antibody specific for HLA-DR and conjugated to PE, and also with a second antibody, the second antibody specific for CD14 and conjugated to the PerCP moiety of a PerCP/CY5.5 tandem fluorophore; the binding of the anti-HLA-DR antibody to the CD14$^+$ cells is then measured, preferably by flow cytometry.

The antibody incubation is preferably performed on an unfractionated—that is, whole blood peripheral—blood sample. Although the methods, reagents, and kits of the present invention may equally be used to assess HLA-DR expression on monocyte-containing peripheral blood fractions, the elimination of antecedent fractionation steps effects a simplification over the protocol used in the reported clinical trial, Kox et al., *Arch. Intern. Med.* 157:389–393 (1997); Döcke et al., *Nature Med.* 3:678–681 (1997); Döcke et al., in Schmitz et al. (eds.), *Durchflusszytometrie in der Klinischen Zelldiagnostic*, Schattauer: Stuttgart and New York (1994), pp. 163–177 (hereinafter collectively "Döcke assay"). Eliminating fractionation steps reduces assay time, reduces potential sample loss, and reduces sources of assay variance, important benefits in an assay intended, in part, for clinical use. Further advantages of whole blood assays are reported in Picker et al., *Blood* 86(4):1408–1419 (1995); Suni et al., *J. Immunol.* 212:89–98 (1998); and Kahan, "Application Note 2: Detecting Intracellular Cytokines in Activated Monocytes," Becton Dickinson Immunocytometry Systems (San Jose) (1997), the disclosures of which are incorporated herein by reference.

As would be apparent, however, the persistence of erythrocytes in the whole blood sample beyond the staining step may complicate later efforts to measure fluorophore bound specifically to the nucleated cells in the sample. Thus, in such circumstances the methods of the present invention may include, after the antibody incubation step and before the flow cytometric acquisition of data, a further step of lysing the erythrocytes in the sample.

A number of agents that serve simultaneously to lyse red blood cells and to fix nucleated cells in a whole blood sample, without interfering with binding of antibody to the nucleated cells, are known in the art. These agents are described, inter alia, in U.S. Pat. Nos. 4,654,312; 4,902,613; 5,510,267; 5,516,695; 5,648,225 and European Patent No. EP 161770 B1, the disclosures of which are incorporated herein by reference. Several such agents are available commercially, including FACS™ Lysing Solution (Becton Dickinson Immunocytometry Systems, San Jose, Calif., catalogue No. 349202) and Whole Blood Lysing Solution (Caltag Laboratories, Inc., Burlingame, Calif., catalogue no. GAS-10).

The minimum duration of incubation with lysis reagent depends upon whether, after lysis, debris is removed by centrifugation.

In the simplest assay protocol, flow cytometric determination of HLA-DR expression is measured directly from the lysed sample, without removal of lysis debris. In this approach, the incubation with lysis reagent may range from about 1–60 minutes, preferably from about 2–30 minutes, more preferably about 10 minutes.

In an alternative protocol in which lysis debris is removed by centrifugation, followed optionally by washing of the mononuclear cell pellet, incubation with lysis reagent is preferably performed for a minimum of about 8–10 minutes prior to centrifugation. In this alternative protocol, incubation ranges from about 8–60 minutes, preferably about 8–30 minutes, most preferably from about 8–15 minutes, with an incubation of about 8–10 minutes most preferable.

Incubation with lysis reagent in either case is performed preferably at room temperature, in accordance with the instructions packaged with the lysis reagent.

Thus, as set forth in Example 1 below, a preferred protocol for measuring HLA-DR expression on the surface of peripheral blood monocytes is as follows:

1) To 50 μl of whole blood add 10 μl of staining reagent. The staining reagent contains
   500 ng of HLA-DR-PE (1:1 Ab:PE ratio)
   63 ng CD14-PerCP/CY5.5
   18 mM chloroquine in buffered saline containing gelatin and 0.1% sodium azide (where, in accordance with convention, HLA-DR-PE and CD14-PerCP/Cy5.5 refer to antibodies with specificity for HLA-DR and CD14, respectively, as conjugated to the indicated fluorophores)
2) Incubate for 25–35 minutes in the dark at room temperature.
3) Add 1 ml 1× FACS™ Lysing Solution (obtained as 10× stock, BDIS catalog No. 349202) and incubate approximately 10 minutes at room temperature in the dark.
4) Analyze directly using a FACS™ brand flow cytometer (BDIS, San Jose, Calif.). Acquire 2000 monocyte events and assess the binding of anti-HLA-DR antibody thereto.

As would be apparent to the skilled artisan, the method for calibrating and running the flow cytometer, as well as the methods for analyzing the data so acquired, can be varied, and such variations are well within the skill in the art.

And as would be further understood, flow cytometers and fluorescence activated cell sorters from other manufacturers can also be used, as can other devices that prove useful in measuring fluorescence from antibody-labeled cells, such as microvolume fluorimeters (volumetric capillary cytometers), such as are described in U.S. Pat. Nos. 5,547,849, 5,556,764, 5,932,428 and 5,912,134, incorporated herein by reference in their entireties.

And as further described in the Examples below, further steps may be performed, such as removal of lysis debris by aspiration of supernatant following collection of the cells by centrifugation, optionally including a further wash of the mononuclear cell pellet.

It will also be apparent that monocytes may, and will preferably, be distinguished not only by the CD14$^+$ fluorescent signal but also by physical properties reported, e.g., by the degree of side scatter and forward scatter. Monocytes may even be distinguished solely on the basis of such physical properties.

Finally, it should be noted that samples should not be left too long diluted at the final step prior to data acquisition; about 6% of the signal is lost in the first hour.

Where the anti-HLA-DR antibody is conjugated to fluorophore at a defined molar ratio, it is possible in the above-described assay to estimate the density distribution of HLA-DR expression on the CD14$^+$ monocyte population, and to report the same as antibodies bound per cell.

Figure 5B:
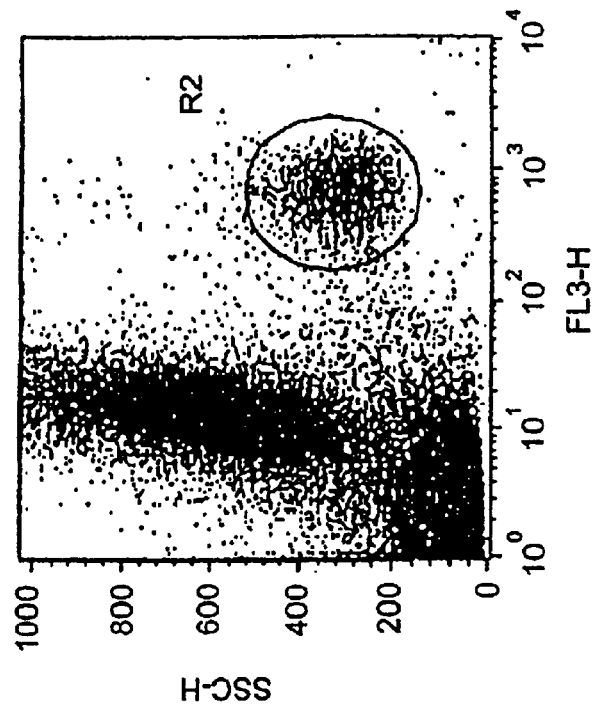
FIG. 5 shows data obtained from a sample of patient peripheral blood using the reagents and methods of the present invention.

As set forth in Example 2, peripheral blood samples were obtained from patients and the density of HLA-DR assayed on monocytes using chloroquine incubation and an anti-CD14-PerCP/CY5.5 conjugate. As further described in the Example, the protocol, in contrast to that presented above, included removal of lysis debris by centrifugation. Samples were also assayed according to the prior Döcke method. Results are shown in FIGS. 5 and 6.

Figure 5A:
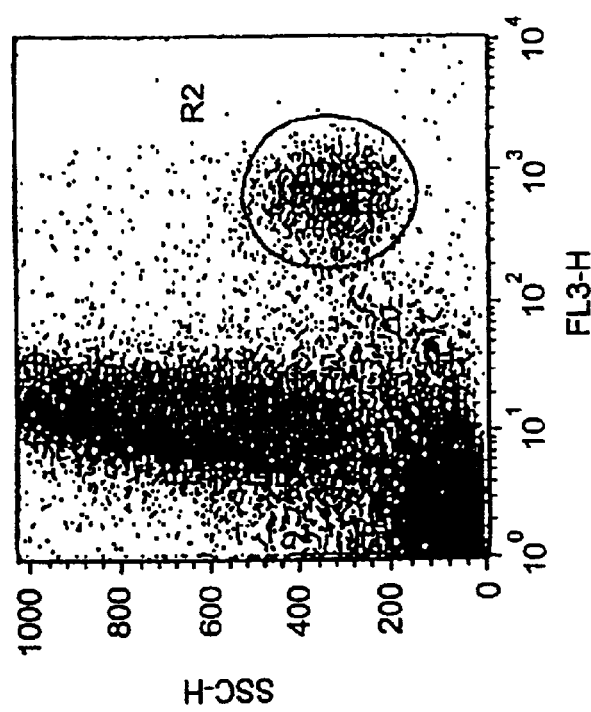
Figures 5C, 5D, 5E, 5F:
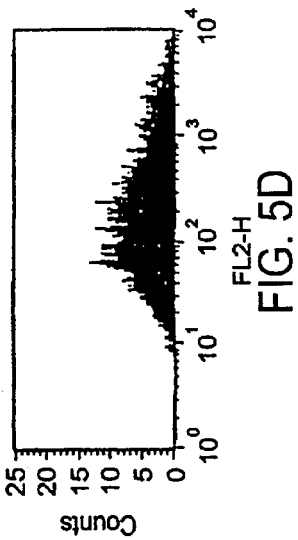

FIG. 5A plots sidescatter (SSC) versus fluorescence channel 3 (CD14-PerCP/CY5.5) for two aliquots of a single patient sample processed according to the method of the present invention. The tightly-clustered CD14$^+$ monocyte population is circled on each. FIG. 5B shows, directly below each dot plot, a histogram charting the PE fluorescence intensity (HLA-DR) measured from the cells in the demarcated monocyte population. Histogram statistics are also given.

Figure 6:
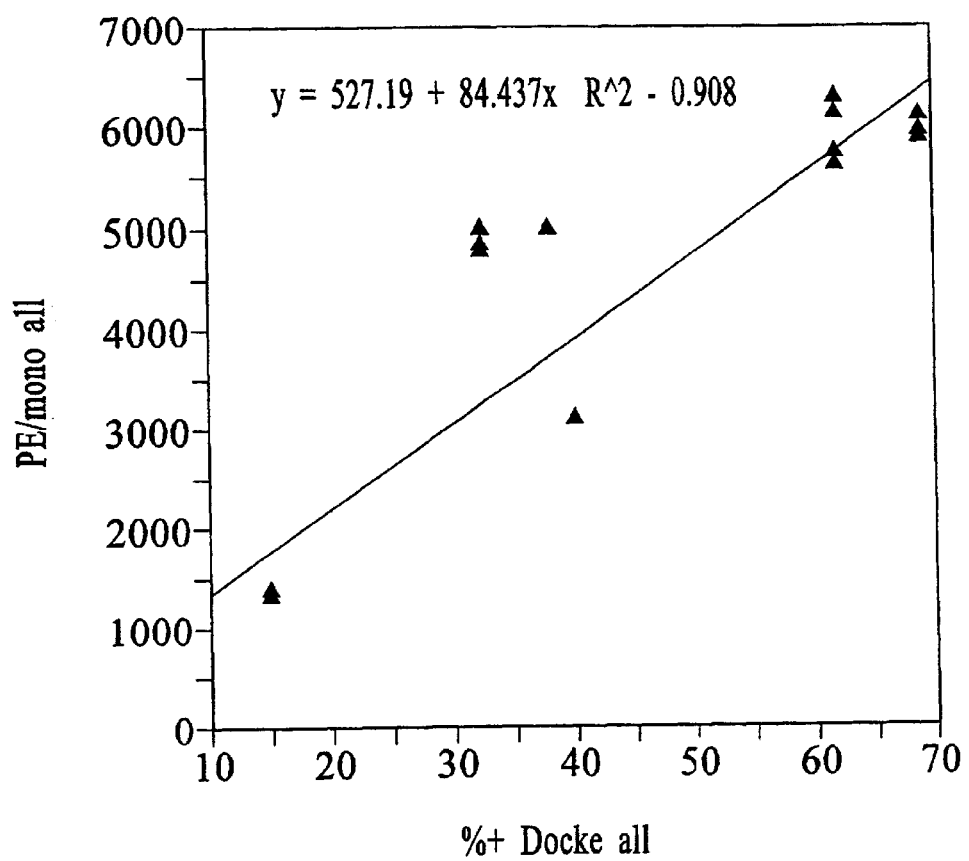
FIG. 6 plots monocytic HLA-DR expression data obtained using the reagents and methods of the present invention against data from the same samples obtained using a prior approach.

FIG. 6 compares the results obtained using methods of the present invention with results obtained using the prior Döcke assay. The y-axis reports number of phycoerythrin molecules (anti-HLA-DR PE) bound on average per monocyte using the present methods; the x-axis reports the percentage of monocytes positive for HLA-DR using the prior methods. Correlation is high, with a correlation coefficient ($r^2$) of 0.908.

To obtain reliable percentages of HLA-DR$^+$ monocytes according to the Döcke method, it was necessary to stain cells using subsaturation levels (approximately 20% saturation) of anti-HLA-DR PE antibody and to monitor the incubation time carefully, both per published protocol. The low degree of antibody saturation, however, means that small variations in antibody concentration lead to large changes in antibody binding, and thus of measured fluorescence. The care with which antibody must be titrated and the degree to which incubation time must be disciplined remove the Döcke assay from the realm of the clinical routineer.

The high correlation between the percentage HLA-DR$^+$ monocytes as measured by the Döcke method and the number of anti-HLA-DR PE molecules bound per monocyte as measured by the methods of the present invention permits the direct translation of the established clinical criteria to measurements reported by the present assay. Thus, as seen in FIG. 6, the prior-established treatment criterion of 30% HLA-DR$^+$ monocytes translates to approximately 3000 molecules PE (anti-HLA-DR) bound per monocyte; similarly, the prior criterion for cessation of treatment, 50% HLA-DR$^+$ monocytes, translates to approximately 4,750 molecules of PE (anti-HLA-DR) bound per cell.

Thus, in another aspect, the present invention provides a method of determining the suitability of immunostimulatory therapy in a patient with sepsis. The method comprises, in its most preferred embodiment, the steps of contacting a peripheral blood sample from the patient with an anti-HLA-DR PE antibody and an anti-CD14-PerCP/CY 5.5 antibody in the presence of chloroquine, then measuring the number of HLA-DR antibodies bound per CD14$^+$ monocyte. Using the prior-established clinical treatment parameters, patients averaging fewer than 3000 anti-HLA-DR antibodies per monocyte for two consecutive days are determined to be suitable for commencement of immunostimulatory treatment, such as treatment with IFN-γ, and treatment is continued until that average density rises to approximately 4700–5000, preferably 5000 or more, anti-HLA-DR molecules per peripheral blood monocyte, preferably for two to three consecutive days.

It will, of course, be understood that with the accumulation of more clinical data, which data will now increasingly be forthcoming given the ease and reliability of the methods of the present invention, that criteria for immunostimulatory treatment of septic patients likely will change. Thus, it should be understood that the present invention provides a general method of determining the suitability of immunostimulatory therapy in a patient with sepsis, wherein the density of HLA-DR expression on the surface of peripheral blood monocytes indicates a measure of immune dysfunction in the patient's professional APC compartment, suitable for remediation by immunostimulatory agents and methods. It will also be understood that IFN-γ, while the presently preferred immunostimulatory agent, will likely be complemented in the future or even superseded by other agents that reverse the dysfunction of the patient's professional APCs. Among such methods are treatment with G-CSF, GM-CSF and dialysis.

As noted, the methods presented herein are of particular utility in the clinical setting. Flow cytometry has now become a routine part of the clinical laboratory, Riley et al., *Clinical Applications of Flow Cytometry*, Igaku-Shoin Medical Publ. (1993); Coon et al. (eds.), *Diagnostic Flow Cytometry* (Techniques in Diagnostic Pathology, No 2), Williams & Wilkins (1991); Keren et al., *Flow Cytometry and Clinical Diagnosis*, Amer. Soc'y of Clinical Pathol. (ISBN 0891893466, 1994), and the methods presented herein are well within the skill of the clinical pathology laboratory.

However, any one clinical laboratory may have only sporadic need to perform the assay, and there is thus a need for compositions and kits that permit the assay readily to be performed on an as-needed basis.

Thus, in another aspect, the present invention provides compositions, hereinafter termed "staining compositions," each comprising fluorophore-conjugated antibody and a lysosomotropic amine. In one embodiment, the staining composition comprises an anti-HLA-DR antibody and a lysosomotropic amine. More preferably, the staining composition further comprises an anti-CD14 antibody; in the most preferred embodiments, the composition comprises anti-HLA-DR-PE, anti-CD14-PerCP/CY5.5, and chloroquine. For measurement of the density of HLA-DR molecules on the surface of monocytes, the anti-HLA-DR antibody is conjugated to PE at a defined molar ratio, most preferably at a molar ratio of 1:1.

It will be understood that these staining compositions may further include various diluents, preservatives and stabilizers standard in the art, such as buffered gelatin and sodium azide.

In yet another aspect, the present invention provides kits for the measurement of HLA-DR on the surface of peripheral blood cells, and in preferred embodiments, on the surface of peripheral blood monocytes.

In one embodiment, the kit comprises a staining composition and an erythrocyte lysing composition. The staining composition, as described above, preferably comprises an anti-HLA-DR antibody and a lysosomotropic amine. More preferably, the staining composition further comprises an anti-CD14 antibody; in the most preferred embodiments, the composition comprises anti-HLA-DR-PE, anti-CD14-PerCP/CY5.5, and chloroquine. For applications in which the density of HLA-DR is to be measured, the anti-HLA antibody of the staining composition of the kit is conjugated to PE at a defined molar ratio, most preferably at a molar ratio of 1:1, and the kit further comprises pelletized beads conjugated with defined levels of PE, to permit the calibration of the flow cytometer.

Figure 7:
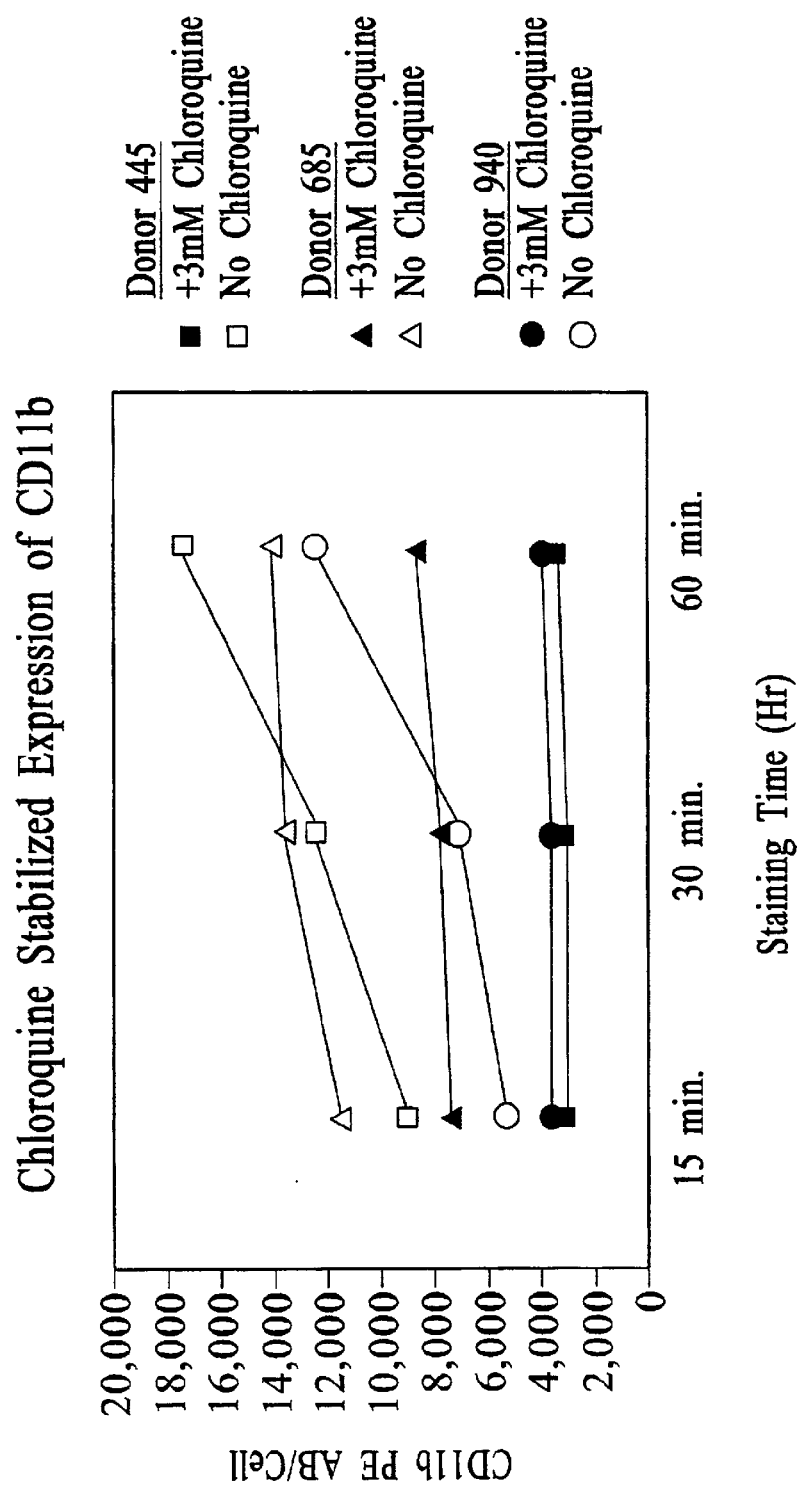
FIG. 7 demonstrates stabilization by chloroquine of CD11b-specific fluorescent signal measured flow cytometrically in a whole blood sample.

As noted above, the basis for the time-dependence of the HLA-DR fluorescence signal during anti-HLA-DR antibody staining is unknown, as is the mechanism by which chloroquine stabilizes the signal over time. But whatever the mechanism, it is clear that it is shared by other cell surface molecules. Thus, FIG. 7 shows that the fluorescence signal produced during antibody staining of CD11b in whole blood samples also increases with staining time, and that the fluorescent signal can similarly be stabilized by addition of chloroquine at 3 mM final concentration. FIG. 7 further demonstrates that these phenomena, as with HLA-DR, can be seen in the blood from donors with quite different average levels of expression.

Thus, in another aspect, the invention provides improved methods, compositions, and kits for measuring CD11b expression on the surface of human blood cells. The method comprises contacting a sample containing human blood cells with a lysosomotropic amine and an antibody specific for CD11b, and then detecting the binding of the CD11b antibody to the cells. The compositions comprise a CD11b-specific antibody, typically conjugated to a fluorophore, and a lysosomotropic amine, typically chloroquine. In one embodiment, the kit comprises a staining composition and an erythrocyte lysing composition. The staining composition, as described above, preferably comprises an anti-CD11b antibody and a lysosomotropic amine. The staining composition can further comprise an anti-CD45 antibody; in the most preferred embodiments, the composition comprises anti-CD11b-PE, anti-CD45 PerCP, and chloroquine.

The following examples are offered by way of illustration and not by way of limitation.

EXAMPLES

In general, and unless otherwise stated, the flow cytometric methods used in the following examples are well known in the art. Detailed protocols are compiled in several recent compendia, including *Flow Cytometry: A Practical Approach*, 2nd ed., M. G. Ormerod (ed.), Oxford University Press, 1997; *Handbook of Flow Cytometry Methods*, J. Paul Robinson (ed.), John Wiley & Sons (1993); *Current Protocols in Cytometry*, J. Paul Robinson (ed.), John Wiley & Sons (October 1997, with periodic updates); *Becton Dickinson Cytometry Source Book*, Becton Dickinson Immunocytometry Systems (1998, with periodic updates)(San Jose, Calif.), the disclosures of which are herein incorporated by reference.

For convenience, antibody designations are abbreviated by indicating antigenic specificity followed by fluorophore. Fluorophore abbreviations are phycoerythrin (PE), peridinin chlorophyll protein (PerCP), allophycocyanin (APC), fluorescein isothiocyanate (FITC), cyanine 5 (CY5) and cyanine 5.5 (CY5.5). Thus, an antibody labeled with phycoerythrin (PE) that is specific for HLA-DR is denominated "HLA-DR PE." Becton Dickinson Immunocytometry Systems (San Jose, Calif.) as the source of reagents is abbreviated "BDIS".

Example 1

Chloroquine Inhibition of Time-Dependent Variation in HLA-DR-Specific Fluorescent Antibody Staining Peripheral blood samples were drawn from normal volunteers.

The time-dependence of the HLA-DR-specific signal detectable by flow cytometry of antibody-stained peripheral blood monocytes was assessed by varying the duration of antibody staining.

For the experiments reported in FIG. 1, to 50 µl EDTA-anticoagulated whole blood was added 10 µl of staining reagent containing either (a) CD14PerCP/CY5.5 (63 ng) and HLA-DR-PE (250 ng) (donors #160 and #325) or (b) CD14-PerCP/CY5.5 (63 ng) and HLA-DR-PE (500 ng) (donor #790).

Samples were incubated with staining reagent at room temperature for the times indicated, after which 1 ml of 1× FACS™ Lysing Solution (10× stock from BDIS, catalog no. 349202) was added, and incubation continued for 10 minutes.

For donor #160, the samples were then centrifuged at 250×g for 5 minutes, the supernatant removed, the pellet resuspended in 2 ml of PBS+0.5% BSA and recentrifuged. The final pellet was suspended in 0.5 ml of PBS+BSA and analyzed by flow cytometry. For donors #790 and #325 the post-lysis wash was omitted: following the incubation with Lysing Solution, the samples were centrifuged at 250×g for 5 minutes, the supernatant removed, and the pellet directly resuspended in 0.5 ml of PBS+BSA for analysis by flow cytometry.

Flow cytometric acquisition of at least 2000 monocyte events was performed for each sample using a FACS™ brand flow cytometer (BDIS) calibrated using CaliBRITE™ (BDIS cat. no. 349502) or QuantiBRITE™ (BDIS cat. no. 340495) beads according to manufacturer's instructions. The PE fluorescence intensity for monocyte-specific events was plotted as shown in FIG. 1.

The effect of various additives on the stability of HLA-DR-specific fluorescence intensity was tested by including these reagents during the staining step.

In a first experiment, the results of which are reported in FIG. 2A, peripheral blood samples (50 µl EDTA-anticoagulated whole blood) were stained with either (a) 10 µl of staining reagent containing 500 ng HLA-DR-PE and 63 ng CD14-PerCP/CY5.5 (reported in the figure as "Control"); (b) 10 µl staining reagent containing 500 ng HLA-DR-PE, 63 ng CD14-PerCP/CY5.5, and 0.6% sodium azide (final azide concentration 0.1%; reported in FIG. 2A as "Azide"); or (c) 10 µl staining reagent containing 500 ng HLA-DR-PE, 63 ng CD14-PerCP/CY5.5, and 18 mM chloroquine (final chloroquine concentration 3 mM; reported in FIG. 2A as "Chloroquine"). Incubation was at room temperature for the times indicated, after which 1 ml of 1× FACS™ Lysing Solution was added and incubation continued for 10 minutes.

Following erythrocyte lysis, the samples were centrifuged at 250×g for 5 minutes, the supernatant removed, the pellet resuspended in 2 ml of PBS+0.5% BSA and recentrifuged. The final pellet was suspended in 0.5 ml of PBS+BSA and analyzed by flow cytometry, as above. Results are plotted in FIG. 2A.

A second experiment, reported in FIG. 2B, was performed similarly, but omitting the post-lysis wash step: following erythrocyte lysis, the samples were centrifuged at 250×g for 5 minutes, the supernatant, containing lysis debris, removed, and the pellet resuspended directly in 0.5 ml of PBS+0.5% BSA. Again, flow cytometric acquisition of at least 2000 monocyte events was performed, and the PE fluorescence intensity of the monocyte population plotted.

To test whether Brefeldin A and monensin would similarly stabilize HLA-DR expression in the flow cytometric assay, an additional series of experiments was performed.

To 50 µl EDTA-anticoagulated whole blood was added 10 µl staining reagent (500 ng of HLA-DR-PE and 63 ng CD14-PerCP/CY5.5 in buffered saline containing gelatin and 0.1% sodium azide); the staining reagent further included the additives noted below. Samples were incubated with staining reagent for the times indicated, after which 1 ml of 1× FACS™ Lysing Solution was added. After incubation with lysing solution for 9.5 to 11.5 minutes, samples were directly analyzed using a FACSCalibur™ brand flow cytometer (BDIS, San Jose, Calif.).

Additives to the staining composition for this latter series of experiments, reported in FIG. 2C, were: (A) nothing ("Control"); (B) 18 mM chloroquine; (C) 0.2 mM Brefeldin A; and (D) 0.013 mM monensin. Final concentrations of additives after 1:6 dilution during staining were: (B) 3 mM chloroquine; (C) 0.034 mM Brefeldin A; and (D) 0.0022mM monensin. Final concentrations of Brefeldin A and monensin are those that have been found sufficient to block processing and secretion of cytokines, per Picker et al., *Blood* 86(4):1408–1419 (1995); Suni et al., *J. Immunol.* 212:89–98 (1998).

The data presented in FIG. 2C were acquired immediately after lysis; in contrast to experiments the results of which are presented in FIG. 1, the removal of lysis debris (by centrifugation and aspiration, optionally followed by wash) was omitted. Independent experiments (not shown) have demonstrated that the results are comparable whether debris is removed or not. When debris removal is not performed, the duration of the lysis step may be shortened: samples can be analyzed as soon as approximately 60 seconds after staining. Samples may be assayed up to about 60 minutes after staining (with loss, over the 60 minutes, of about 5–10% HLA-DR-PE fluorescence).

As shown in FIGS. 2A–2C, chloroquine—but not azide, Brefeldin A or monensin—reliably stabilized HLA-DR fluorescence, with signals at 60 minute incubation substantially identical to those at 10–15 minutes incubation. In experiments not shown, hydroxychloroquine was shown equally effective in stabilizing HLA-DR signal as chloroquine.

A further experiment was performed to determine the minimum concentration of chloroquine needed to effect stabilization of HLA-DR expression on the surface of monocytes.

An aliquot of 50 μl peripheral blood was drawn from a healthy volunteer and mixed with 10 μl HLA-DR quantitation reagent (50 μg/ml HLA-DR PE, 6.3 μg/ml CD14 PerCP-Cy5.5, in 10 mM sodium pyrophosphate, 0.15 M NaCl, pH 8). The HLA-DR quantitation reagent further contained chloroquine at 0 mM (control), 6 mM, 12 mM, or 18 mM.

In each experiment, 4 blood samples were stained for each chloroquine level, with one each of the samples stained for 20, 40, 60 or 80 minutes.

At the end of the staining period, the samples were lysed with 1× FACS™ Lysing Solution (BDIS) and analyzed on a FACScalibur Flow Cytometer. Five hundred monocyte events were collected. The HLA-DR PE median (FL2) was determined from a histogram which was gated on the monocyte population in FL3\side scatter. Results, shown in FIGS. 2D and 2E, demonstrate that HLA-DR stabilization may be obtained with chloroquine at 2 mM or above, but that 1 mM chloroquine was insufficient to effect stabilization.

Example 2

Measurement of HLA-DR on Patient Peripheral Blood Monocytes

Peripheral blood samples were obtained by venipuncture from patients admitted to ICU. One aliquot of each sample was assayed using the following protocol.

To 50 μl of whole blood was added 10 μl of staining reagent containing 50g/ml HLA-DR-PE (clone L243); 6.3 μg/ml CD14-PerCP/CY5.5; and 18 mM chloroquine diphosphate. HLA-DR-PE (BDIS cat. no. 347367, repurified to provide a 1:1 antibody:PE conjugate) is a mouse $IgG_{2a}/\kappa$ antibody that reacts with a nonpolymorphic HLA-DR epitope and does not cross-react with HLA-DQ or HLA-DP molecules. CD14-PerCP/CY5.5 (BDIS custom conjugate of antibody LeuM3, available unconjugated as BDIS catalogue number 347490) is a mouse $IgG_{2b}/\kappa$ antibody specific for CD14.

The aliquot was incubated for 25–35 minutes in the dark at room temperature, and then 1 ml 1× FACS™ Lysing Solution (obtained as 10× stock, BDIS catalog No. 349202) was added and incubation continued for 8–10 minutes. The cells were then collected by centrifugation at 300×g (1200 RPM in a Sorvall 6000 centrifuge) and the lysis debris in the supernatant aspirated. The cell pellet was resuspended in 0.5 ml PBS containing 0.5% bovine serum albumin (BSA).

The sample was analyzed using a FACS™ brand flow cytometer. Calibration was performed using Quan-tiBRITE™ quantitation kit (BDIS cat. no. 340495). A minimum of 2000 monocyte events ($CD14^+$ and further delimited based on side scatter) were acquired, and PE fluorescence of these cells charted. FIG. 5 shows the data collected on one such patient sample.

A second aliquot of each sample was fractionated over Ficoll-Hypaque and the PBMC assayed according to Kox et al., Arch. Intern. Med. 157:389–393 (1997); Döcke et al., Nature Med. 3:678–681 (1997); and Docke et al., in Schmitz et al. (eds.), Durchflusszytometrie in der Klinischen Zelldiagnostic, Schattauer: Stuttgart and New York (1994), pp. 163–177.

Results for each sample by both methods are plotted in FIG. 6 as filled triangles. The best-fit linear regression line through the points is shown.

Example 3

Stabilization of CD11b-Specific Fluorescent Signal by Chloroquine

Blood from three normal adult donors was collected in standard EDTA Vacutainer® tubes and placed directly on ice. Fifty (50) μl of whole blood was transferred to a tube containing 20 μl of a cocktail of CD11b PE and CD45 PerCP antibodies with or without chloroquine, with the chloroquine-containing tubes having a final chloroquine concentration of 3 mM. Blood was stained for the indicated time at room temperature before addition of 1.0 ml FACS lysing reagent (1×). Flow cytometric analysis was performed essentially as described in Examples 1 and 2. Results are shown in FIG. 7.

All patents, patent publications, and other published references mentioned herein are hereby incorporated by reference in their entirety as if each had been individually and specifically incorporated by reference herein. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

What is claimed is:

1. A composition for flow cytometric measurement of a cell-surface molecule on human peripheral blood cells, wherein said cell-surface molecule is characterized in that a fluorescent signal measured following staining with a fluorescently labeled antibody specific for said cell-surface molecule in the absence of a lysosomotropic amine depends on the time of incubation with said antibody, said composition comprising:

a fluorophore-conjugated antibody specific for said cell-surface molecule, and a lysosomotropic amine.

2. The composition of claim 1, wherein said lysosomotropic amine is selected from the group consisting of chloroquine, hydroxychloroquine, primaquine, and methylamine.

3. The composition of claim 2, wherein said lysosomotropic amine is chloroquine.

4. The composition of claim 2, wherein said lysosomotropic amine is hydroxychloroquine.

5. The composition of claim 1, wherein said fluorophore is PE.

6. The composition of claim 5, wherein said PE fluorophore and said antibody are conjugated at a defined molar ratio.

7. The composition of claim 6, wherein said ratio is 1:1.

8. A kit for flow cytometric measurement of a cell-surface molecule on the surface of peripheral blood cells, comprising:

a composition according to claim 1, and an erythrocyte lysing composition.

9. The kit according to claim 8, further comprising: pelletized beads conjugated with defined levels of PE.

* * * * *